(12) United States Patent
Niwa et al.

(10) Patent No.: US 7,838,912 B2
(45) Date of Patent: Nov. 23, 2010

(54) SEMICONDUCTOR SENSING FIELD EFFECT TRANSISTOR, SEMICONDUCTOR SENSING DEVICE, SEMICONDUCTOR SENSOR CHIP AND SEMICONDUCTOR SENSING DEVICE

(75) Inventors: Daisuke Niwa, Tokyo (JP); Ichiro Koiwa, Tokyo (JP); Tetsuya Osaka, Tokyo (JP)

(73) Assignee: Waseda University, Tokyo (JP)

( * ) Notice: Subject to any disclaimer, the term of this patent is extended or adjusted under 35 U.S.C. 154(b) by 312 days.

(21) Appl. No.: 11/660,514

(22) PCT Filed: Mar. 11, 2005

(86) PCT No.: PCT/JP2005/004288

§ 371 (c)(1),
(2), (4) Date: Feb. 20, 2007

(87) PCT Pub. No.: WO2006/038324

PCT Pub. Date: Apr. 13, 2006

(65) Prior Publication Data

US 2008/0012049 A1 Jan. 17, 2008

(30) Foreign Application Priority Data

Sep. 30, 2004 (JP) ............................... 2004-287286
Nov. 12, 2004 (JP) ............................... 2004-329172

(51) Int. Cl.
*C12Q 1/00* (2006.01)
(52) U.S. Cl. .................. 257/253; 257/315; 257/414; 257/E29.242; 257/E21.159; 257/E29.255; 257/E21.409; 435/4; 435/287.1; 438/49; 436/528; 436/40; 204/164; 324/71.5
(58) Field of Classification Search ..................... None
See application file for complete search history.

(56) References Cited

U.S. PATENT DOCUMENTS 4,881,109 A * 11/1989 Ogawa ........................ 257/253

(Continued)

FOREIGN PATENT DOCUMENTS

EP 0173356 A2 3/1986

(Continued)

OTHER PUBLICATIONS

Daisuke Niwa et al., Japanese Journal of Applied Physics vol. 43, No. 1A/B, pp. L105-L107.

(Continued)

*Primary Examiner*—Victor A Mandala
*Assistant Examiner*—Fei Fei Yeung Lopez
(74) *Attorney, Agent, or Firm*—Birch, Stewart, Kolasch & Birch, LLP

(57) ABSTRACT

A semiconductor sensing field effect transistor uses an organic unimolecular film formed on a gate insulating layer. In the semiconductor sensing field effect transistor and a semiconductor sensing device, the gate insulating layer has a stack structure wherein a second silicon oxide layer is stacked on a first silicon oxide layer through a silicon nitride layer. A semiconductor sensor chip and the semiconductor sensing device are provided with a field effect transistor chip wherein the gate insulating layer, a source electrode and a drain electrode are integrated on a silicon board, a source electrode terminal wiring connected with the source electrode, and a drain electrode terminal wiring connected with the drain electrode. In the semiconductor sensor chip and the semiconductor sensing device, the transistor chip, the source electrode terminal wiring and the drain electrode terminal wiring are sealed so as to expose an edge part which is not connected with the gate insulating layer of the transistor chip and the source electrode of the source electrode terminal wiring, and an edge part which is not connected with the drain electrode of the drain electrode terminal wiring.

10 Claims, 29 Drawing Sheets

U.S. PATENT DOCUMENTS

| | | | |
|---|---|---|---|
| 5,066,383 A * | 11/1991 | Yamaguchi et al. | 204/435 |
| 5,153,818 A | 10/1992 | Mukougawa et al. | |
| 5,663,589 A * | 9/1997 | Saitoh et al. | 257/401 |
| 5,698,879 A * | 12/1997 | Aritome et al. | 257/315 |
| 6,222,224 B1 * | 4/2001 | Shigyo | 257/315 |
| 6,921,782 B2 * | 7/2005 | Matsushima | 523/457 |
| 2001/0044119 A1 * | 11/2001 | Ghadiri et al. | 435/7.1 |
| 2002/0167003 A1 * | 11/2002 | Campbell et al. | 257/40 |
| 2004/0109884 A1 * | 6/2004 | Burmeister et al. | 424/423 |
| 2004/0175871 A1 | 9/2004 | So | |
| 2005/0170347 A1 | 8/2005 | Miyahara et al. | |
| 2008/0012049 A1 | 1/2008 | Niwa et al. | |

FOREIGN PATENT DOCUMENTS

| | | |
|---|---|---|
| JP | 64-61660 A | 3/1989 |
| JP | 4-8596 A | 1/1992 |
| JP | 06-273378 A | 9/1994 |
| JP | 07-159366 A | 6/1995 |
| JP | 09-166571 A | 6/1997 |
| JP | 11-51895 A | 2/1999 |
| JP | 2002-340849 A | 11/2002 |
| JP | 2002-350387 A | 12/2002 |
| JP | 2003-270241 A | 9/2003 |
| JP | 2004-4007 A | 1/2004 |
| JP | 2004-117073 A | 4/2004 |
| JP | 2004-184255 A | 7/2004 |
| JP | 2005-91014 A | 4/2005 |
| JP | 2005-218310 A | 8/2005 |

OTHER PUBLICATIONS

Extended Abstracts (The 66th Autumn Meeting, 2005), The Japan Society of Applied Physics, JSAP Catalog No. AP 051133-03, No. 3, pp. 1-4.

Martin et al., "Liquid Mechanical Behavior of Mixed Monolayers of Amino and Alkyl Silanes by Atomic Force Microscopy", Langmuir, 2005, pp. 6934-6943, vol. 21, American Chemical Society.

Motohashi et al., "Detection of Hybridization Reaction of DNA Using Monolayer Modified Field Effect Transistor", Jpn. J. Appl. Phys., 2004, vol. 43.

Niwa et al., "Formation of Micro and Nanoscale Patterns of Monolayer Templates for Position Selective Immobilization of Oligonucleotide Using Ultraviolet and Electron Beam Lithography", Chemistry Letters, 2004, pp. 176-177, vol. 33, No. 2, The Chemical Society of Japan.

Niwa et al., "Organosilane Self-Assembled Monolayer-Modified Field Effect Transistors for On-Chip Ion and Biomolecule Sensing", Sensors and Actuators, vol. 108, 2005, pp. 721-726, Elsevier B.V.

U.S. Office Action in related U.S. Appl. No. 11/514,843 dated Jun. 1, 2009.

U.S. Office Action in related U.S. Appl. No. 11/514,843, dated Dec. 3, 2009.

U.S. Restriction Requirement in related U.S. Appl. No. 11/514,843 dated Feb. 20, 2009.

* cited by examiner

(A)

(B)

(C)

(A)

(B)

(C)

(D)

(A)

(B)

(C)

(D)

(A)

(B)

(C)

(A)

(B)

(C)

(D)

(A)

(B)

(A)

(B)

(C)

(A)

(B)

(C)

(A)

(B)

(A)

(B)

(A)

(B)

(A)

(B)

(A)

(B)

(C)

(A)

(B)

(C)

(A)

(B)

(A)

(B)

(A)

(B)

(C)

(D)

(A)

(B)

(C)

(D)

(A)

(B)

(C)

(A)

(B)

(A)

(B)

(C)

(A)

(B)

(C)

(A)

(B)

(C)

(A)

(B)

(C)

(A)

(B)

(A)

(B)

(C)

(A)

(B)

(A)

(B)

(C)

SEMICONDUCTOR SENSING FIELD EFFECT TRANSISTOR, SEMICONDUCTOR SENSING DEVICE, SEMICONDUCTOR SENSOR CHIP AND SEMICONDUCTOR SENSING DEVICE

TECHNICAL FIELD

This invention relates to a field effect transistor for use in semiconductor sensing suitable for ion sensing and bio-sensing, and more particularly, to a field effect transistor for use in semiconductor sensing effective in bio-micro systems and micro-chemical analysis systems, and a semiconductor sensing device using the same.

This invention also relates to a semiconductor sensor chip which is advantageously used in ion sensing and bio-sensing, and effective in bio-micro systems and micro-analysis systems, and more particularly, to a semiconductor sensor chip which is advantageous for liquid analysis on practical use due to sufficient water- and liquid-proofness, and a semiconductor sensing device.

BACKGROUND ART

Ion sensing systems and bio-sensing systems are applied to a wide variety of fields including food preparation and management, environmental measurement and the like. In the ion and bio-sensing areas, there is an increasing demand for ionic and molecular level sensing such as single molecule recognition and single base recognition, and systems and devices with such a sensing ability are needed. For micro-measurement or simultaneous multi-element measurement, there is a need for miniaturization, integration, and on-chip design of such systems and devices.

A typical example of ion sensing device is an ion-sensitive field effect transistor (ISFET) having a silicon nitride film/silicon oxide film/silicon structure. The prior art device uses a separate glass electrode as the reference electrode for pH measurement, having not succeeded in miniaturization and on-chip design. In the present status, a silicon nitride film having a thickness as large as 100 to 200 nanometers (nm) is used as the ion-sensitive film.

In the enzyme, immunity and DNA sensing, on the other hand, sensing based on fluorescence and luminescence using laser scanners has become the main stream. In the recent years, attempts have been made to detect electric current and potential through electrochemical reaction. Also with respect to semiconductor detection, only a few examples pertain to the fabrication of enzyme and immunity sensors combined with the above-mentioned ISFET. The basic detection stance taken in these sensors relies on the quantitative effect to enable detection, typically by increasing the effective surface area of a reactive site or electrode site and by increasing the amount of reactant. Also, the detection using laser scanners and the electrochemical detection suffer from problems since there is a tendency that the response sensitivity (strength, response speed or the like) decreases with a progress of integration and miniaturization.

As discussed above, the prior art techniques are awkward to meet the needs including on-chip design, miniaturization and integration. It is thus believed that an innovative improvement is necessary in order to take advantage of single molecule or ion recognition and detection to the maximum extent. Further, in the ion sensing system and bio-sensing system, there is a particular need for a semiconductor device which is designed for in-solution measurement in the state that a sensor is immersed in liquid so that the detector section is kept in contact with the liquid for a long period of time.

As to the field effect transistor (FET), the inventors reported in Jpn. J. Appl. Phys., Vol. 43, No. 1A/B, 2004, pp. L105-107 (Non-patent Reference 1) a field effect transistor having a gate length of 10 μm and a gate width of 1 mm using a silicon substrate (P—Si(100), 8-12 Ωcm).

This FET has a silicon oxide film formed as a gate dielectric layer as shown in FIG. 19C. Such a FET is prepared by first dry oxidizing a silicon substrate 500, which has been pre-cleaned with 1% HF aqueous solution for about 30 seconds, at a temperature of 1000° C., to form a $SiO_2$ film (field oxide film) 501 of 100 nm thick on the surface of silicon substrate 500 (FIG. 17A). A resist is coated on $SiO_2$ film 501 and patterned (exposed and developed) with UV to form a resist pattern 502 at selected areas (FIG. 17B). Using resist pattern 502 as a mask, $SiO_2$ film 501 is etched with 1% HF aqueous solution to such an extent that a lower layer of $SiO_2$ film 501 is left behind (FIG. 17C). The resist pattern 502 is stripped, forming a channel-gate portion 501a (FIG. 17D).

Next, an aluminum film (thickness 300 nm) was deposited by evaporation (ultimate vacuum $2.0 \times 10^{-6}$ Torr, current value 30 mA, deposition rate −5 nm/sec). By a photoresist process, the aluminum film is formed into a predetermined aluminum film pattern 503 (FIG. 18A), which functions as a mask for subsequent ion implantation. By ion implantation (P-dope, 40 kV, $1.0 \times 10^{15}$ ions/cm$^2$) using aluminum film pattern 503 as a mask, N-channels 504, 504 are formed in predetermined areas of an upper layer of silicon substrate 500. The aluminum film pattern 503 is stripped off (by immersing in 50% phosphoric acid at 80° C. for 5 minutes).

After aluminum film pattern 503 is stripped off (FIG. 18B), the surface of $SiO_2$ film 501 is annealed in a $N_2$ atmosphere (900° C., 5 min) for activation. A resist is then coated on $SiO_2$ film 501 and patterned (exposed and developed) with UV to form a resist pattern 505 which cover areas of $SiO_2$ film 501 other than the areas in register with N-channels 504, 504 (FIG. 18C). The $SiO_2$ film 501 on N-channels 504, 504 is etched (1% HF aqueous solution) using resist pattern 505 as a mask, and resist pattern 505 is removed, forming contact holes 504a, 504a (FIG. 18D).

Next, an electrode metallization 506 is formed by evaporation (EB evaporation, ultimate vacuum $2.0 \times 10^{-8}$ Torr). Specifically, a titanium film (thickness 20 nm, vacuum during deposition $4.0 \times 10^{-8}$ Torr, current value 70 mA, deposition rate 0.13 nm/sec) and a platinum film (thickness 120 nm, vacuum during deposition $8.0 \times 10^{-8}$ Torr, current value 220 mA, deposition rate 0.067 nm/sec) are deposited to form electrode metallization 506 (FIG. 19A), which is annealed in a nitrogen atmosphere (800° C., 10 min) to produce $TiSi_2$ at the junction between the Ti film of electrode metallization 506 and N-channels 504, 504, forming contacts.

Then a protective oxide film 507 (thickness 200 nm) is formed on electrode metallization 506 by plasma enhanced CVD (PECVD, 200 W, 400° C., 0.39 Torr, tetraethoxysilane (TEOS) 6 sccm, $O_2$ 100 sccm) (FIG. 19B). Structural recovery treatment is carried out on the CVD oxide film by annealing in an oxygen atmosphere (800° C., 10 min). Gate/electrode contact holes 508, 508 are perforated by reactive ion etching (RIE) with $CHF_3$ gas, yielding a field effect transistor as shown in FIG. 19C.

When such a FET is used as a semiconductor sensing device, it is modified on the gate dielectric layer with an organic monomolecular film or the like. Since a sensor of the type shown in FIG. 19C has the structure that the gate dielectric layer composed of the silicon oxide film is exposed, entry of moisture, ions and the like can impair the transistor characteristics. This sensor is unsuited for long-term measurement with the detector section kept in contact with liquid.

Further, in the ion sensing system and bio-sensing system, for example, there is a particular need for a semiconductor device which is designed for in-solution measurement in the state that not only the sensor section, but also a meter section for measuring the electric signal detected by the sensor section are kept in contact with the liquid for a long period of time.

Especially in the medical field where an ever increasing demand for semiconductor sensors is expected in the future, a possibility of cleaning the sensor section for reuse is low from the safe hygienic aspect. Nevertheless, based on the presumption that the electronic part is brought in contact with liquid such as aqueous solution, prior art semiconductor sensing devices are assembled integral from the water- and liquid-proof standpoint so that the sensor section and the meter section are not readily detachable. The operation of exchanging the sensor section is so complex that disposable instruments are unfeasible.

Further, in order that the sensor section and the meter section be readily detachable, the water- and liquid-tightness at the joint between the sensor section and the meter section is also important in a semiconductor sensing system for which water- and liquid-proofness is required. In the case of disposable instruments in which the sensor section and the meter section are readily detachable so that the sensor section is replaced on every use, tight closure is necessary because entry of moisture or the like through the joint can cause failure of the instrument. For a semiconductor sensor which is susceptible to failure by external forces, a tight closure method matching with the strength thereof is required.

Patent Reference 1:
JP-A 2004-4007
Non-Patent Reference 1:
Daisuke Niwa et al., Jpn. J. Appl. Phys.,
Vol. 43, No. 1A/B, 2004, pp. L105-107

DISCLOSURE OF THE INVENTION

Problem to Be Solved by the Invention

The present invention has been made under the above-discussed circumstances, and its first object is to provide a semiconductor sensing field effect transistor which prevents transistor characteristics from being degraded by entry of moisture and ions through the gate dielectric layer, and is especially suited for in-liquid measurement; and a semiconductor sensing device using the same.

A second object of the invention is to provide a semiconductor sensor chip and a semiconductor sensing system in which the sensor section and the meter section are readily detachable so that the sensor section is disposable, and which is highly feasible in that it has sufficient water-and liquid-proofness to ensure liquid analysis.

Means for Solving the Problem

As discussed above, the field effect transistors for use in semiconductor sensing are of the construction that silicon oxide is present on semiconductor and an organic monomolecular film serving as a direct detector section can be formed on the silicon oxide. In order for semiconductor sensing devices to have an ultimate sensitivity, it is effective that semiconductor is contiguous to silicon oxide, and the silicon oxide is contiguous to an organic monomolecular film.

The invention, in a first aspect that attains the first object, provides a semiconductor sensing field effect transistor comprising a gate dielectric layer formed on silicon, which is to be used as a semiconductor sensing device after an organic monomolecular film is formed on said gate dielectric layer as a direct detector section, characterized in that said gate dielectric layer has a multilayer structure including, in sequence, a first silicon oxide layer, a silicon nitride layer, and a second silicon oxide layer; and a semiconductor sensing device having an organic monomolecular film/gate dielectric layer/semiconductor structure wherein an organic monomolecular film is formed on said gate dielectric layer of the semiconductor sensing field effect transistor as a direct detector section.

In the semiconductor sensing field effect transistor, the gate dielectric layer has a multilayer structure including, in sequence, a first silicon oxide layer, a silicon nitride layer, and a second silicon oxide layer, that is, silicon oxide/silicon nitride/silicon oxide multilayer structure. Then the silicon nitride layer blocks moisture and ions from entering the transistor section through the gate dielectric layer, and the gate dielectric layer has silicon oxide present on both the silicon side and the organic monomolecular film side, thus maintaining compatibility with the organic monomolecular film. There is available a semiconductor sensing device which has a sensing function equivalent to the prior art gate dielectric layer consisting of silicon oxide monolayer.

The invention, in a second aspect that attains the second object, provides a-semiconductor sensor chip comprising a field effect transistor chip having a gate dielectric layer, a source electrode, and a drain electrode integrated on a silicon substrate, a source electrode terminal wiring connected to said source electrode, and a drain electrode terminal wiring connected to said drain electrode, characterized in that said field effect transistor chip, said source electrode terminal wiring, and said drain electrode terminal wiring are sealed with an encapsulant or with a board on which said field effect transistor chip, said source electrode terminal wiring, and said drain electrode terminal wiring are disposed and an encapsulant, such that the gate dielectric layer of said field effect transistor chip, an end portion of said source electrode terminal wiring which is not connected to the source electrode, and an end portion of said drain electrode terminal wiring which is not connected to the drain electrode are exposed; and a semiconductor sensing system comprising the semiconductor sensor chip defined above, and a measuring instrument having electric signal input/output terminals which are detachably connected to the exposed portions of the source electrode terminal wiring and the drain electrode terminal wiring of said semiconductor sensor chip directly or via anisotropic conductive rubber, said measuring instrument being connected to said semiconductor sensor chip for measuring the electric signal detected by said field effect transistor chip.

The semiconductor sensor chip of the invention does not include a section to function as a measuring instrument, but is basically composed of a FET chip, a source electrode terminal wiring, and a drain electrode terminal wiring which are essential as a sensor section. Accordingly, this semiconductor sensor chip allows for more practical disposal of the sensor section. Also since the FET which is a microscopic precision part and the fine source electrode terminal wiring and drain electrode terminal wiring connected thereto are sealed with an encapsulant or with a board on which the FET chip, the source electrode terminal wiring, and the drain electrode terminal wiring are disposed and an encapsulant, the semiconductor sensor chip is endowed with a sufficient strength necessary to handle it.

In the semiconductor sensor chip of the invention, the gate dielectric layer of the FET which should be exposed to the outside for its function, the source electrode terminal wiring and the drain electrode terminal wiring constituting a conductive path for electric signals detected by the semiconductor sensor chip to a measuring instrument are exposed to the outside. By connecting ends of the source electrode terminal wiring and the drain electrode terminal wiring to electric signal input/output terminals, a semiconductor sensing system including the sensor section and the measuring instrument section is constructed. Semiconductor sensing becomes possible when an organic monomolecular film is formed on the gate dielectric layer of the FET as a direct detector section and the detector section is contacted with a test liquid.

Particularly when the exposed end portions of the source electrode terminal wiring and drain electrode terminal wiring are connected to the electric signal input/output terminals via anisotropic conductive rubber, not only electric conduction is ensured by the conductivity of anisotropic conductive rubber, but also the anisotropic conductive rubber affords closer contact due to its elasticity and a buffer action for the compressive force of connecting in close contact the semiconductor sensor chip which is less resistant to external forces. Then more reliable and stable conduction is established between the sensor chip and the measuring instrument.

A first preferred embodiment of the invention provides a semiconductor sensor chip comprising a field effect transistor chip having a gate dielectric layer, a source electrode, and a drain electrode integrated on a silicon substrate, said field effect transistor chip being buried in a recess formed on a board, a source electrode terminal wiring pattern connected to said source electrode through one lead wire, and a drain electrode terminal wiring pattern connected to said drain electrode through another lead wire, the wiring patterns being formed on said board, characterized in that said field effect transistor chip, said source electrode terminal wiring pattern, said drain electrode terminal wiring pattern, and said one and other lead wires are sealed between the upper surface of said board and an encapsulant layer such that the gate dielectric layer of said field effect transistor chip, an end portion of said source electrode terminal wiring pattern which is not connected to the source electrode, and an end portion of said drain electrode terminal wiring pattern which is not connected to the drain electrode are exposed; and a semiconductor sensing system comprising the semiconductor sensor chip defined above, and a measuring instrument having electric signal input/output terminals which are detachably connected to the exposed portions of the source electrode terminal wiring pattern and the drain electrode terminal wiring pattern of said semiconductor sensor chip directly or via anisotropic conductive rubber, said measuring instrument being connected to said semiconductor sensor chip for measuring the electric signal detected by said field effect transistor chip.

A second preferred embodiment of the invention provides a semiconductor sensor chip comprising a field effect transistor chip having a gate dielectric layer, a source electrode, and a drain electrode integrated on a silicon substrate, said field effect transistor chip being buried in a recess formed on a board, a source electrode terminal wiring pattern connected to said source electrode through one lead wire, and a drain electrode terminal wiring pattern connected to said drain electrode through another lead wire, the wiring patterns being formed on said board, characterized in that said field effect transistor chip, said source electrode terminal wiring pattern, said drain electrode terminal wiring pattern, and said one and other lead wires are sealed between the upper surface of said board and an encapsulant layer such that the gate dielectric layer of said field effect transistor chip is exposed, and said source electrode terminal wiring pattern includes an interconnecting extension which passes through said board in a thickness direction, connects to said source electrode terminal wiring pattern, and includes an end portion exposed on the lower surface side of said board, and said drain electrode terminal wiring pattern includes an interconnecting extension which passes through said board in a thickness direction, connects to said drain electrode terminal wiring pattern, and includes an end portion exposed on the lower surface side of said board; and a semiconductor sensing system comprising the semiconductor sensor chip defined above, and a measuring instrument having electric signal input/output terminals which are detachably connected to the exposed portions of the interconnecting extension from the source electrode terminal wiring pattern and the interconnecting extension from the drain electrode terminal wiring pattern of said semiconductor sensor chip directly or via anisotropic conductive rubber, said measuring instrument being connected to said semiconductor sensor chip for measuring the electric signal detected by said field effect transistor chip.

In the first and second preferred embodiments, a higher strength is available because the FET chip and the source electrode terminal wiring and drain electrode terminal wiring are secured and sealed on the board. Since the FET chip is buried in a recess formed on the board and the source electrode terminal wiring and drain electrode terminal wiring are formed as wiring patterns on the board, the surface to be sealed with an encapsulant is substantially flat. Then these semiconductor sensor chips are advantageous in that for the sealing with encapsulant, a method involving applying a UV-curable resin composition, for example, by such techniques as screen printing, and curing the composition may be employed.

BENEFITS OF THE INVENTION

According to the invention, there is provided a semiconductor sensing device which can block entry of moisture and ions into the transistor section through the gate dielectric layer, is especially suited for in-liquid measurement, and exhibits a high detection sensitivity; and a field effect transistor used therein.

According to the invention, the sensor section and the meter section are readily detachable, and the sensor section is disposable. Also, a semiconductor sensor chip and a semiconductor sensing system are provided which are highly feasible in that they have sufficient water- and liquid-proofness to ensure liquid analysis.

Figure 1:
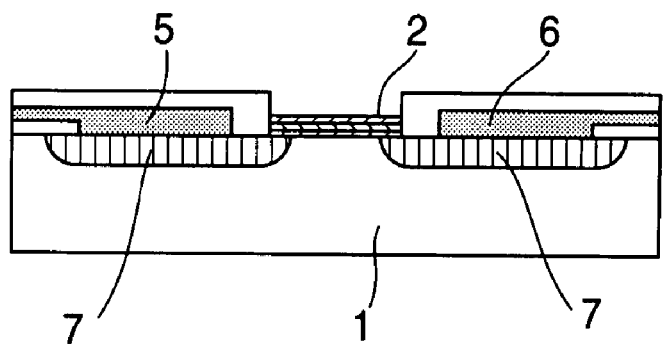
FIG. 1 is a cross-sectional view of a semiconductor sensing FET and semiconductor sensing device according to one embodiment (first embodiment) of the invention (first aspect).
Figure 1:
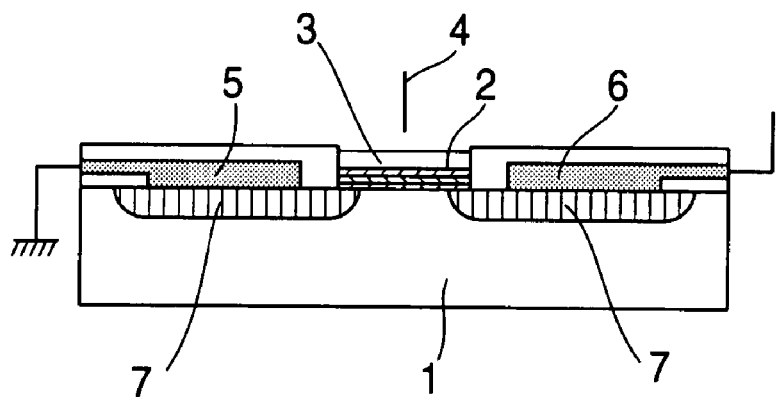
Figure 1:
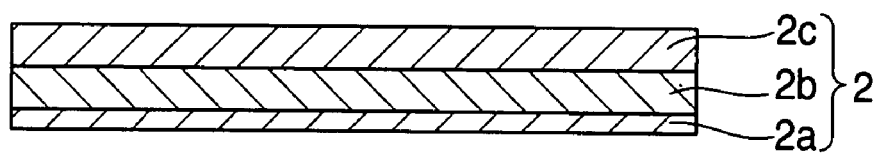
Figure 2:
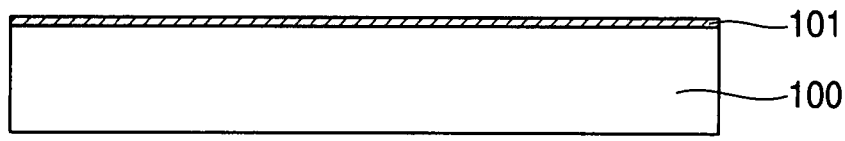
FIG. 2 is a cross-sectional view for illustrating a step (isolating step) in the preparation of a semiconductor sensing FET according to one embodiment (second embodiment) of the invention (first aspect).
Figure 2:
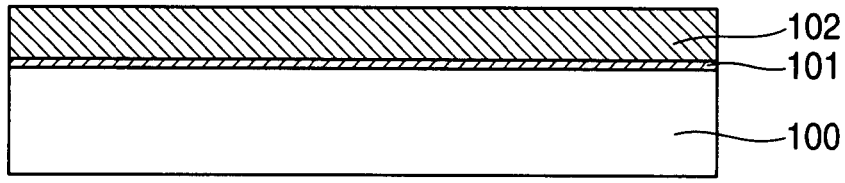
Figure 2:
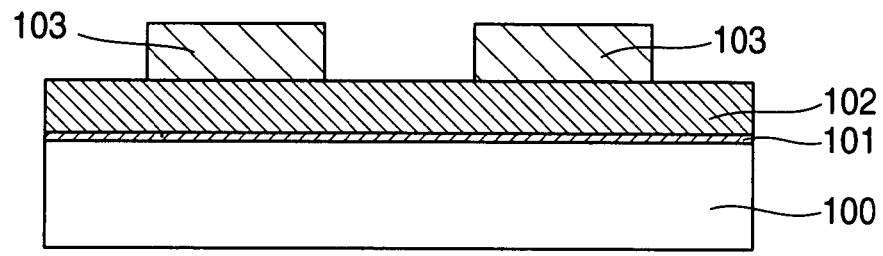
Figure 2:
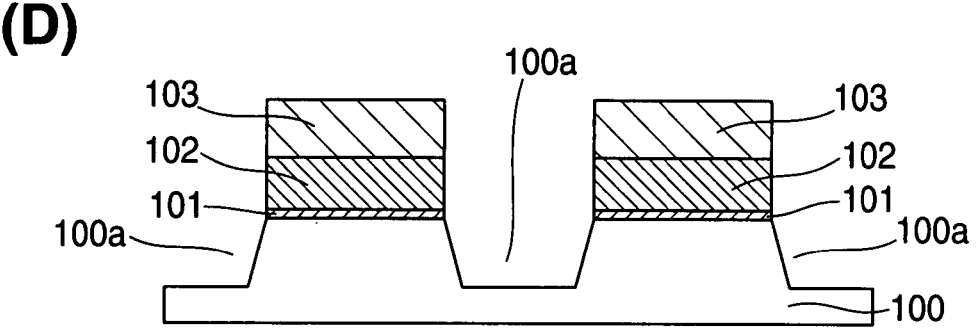
Figure 3:
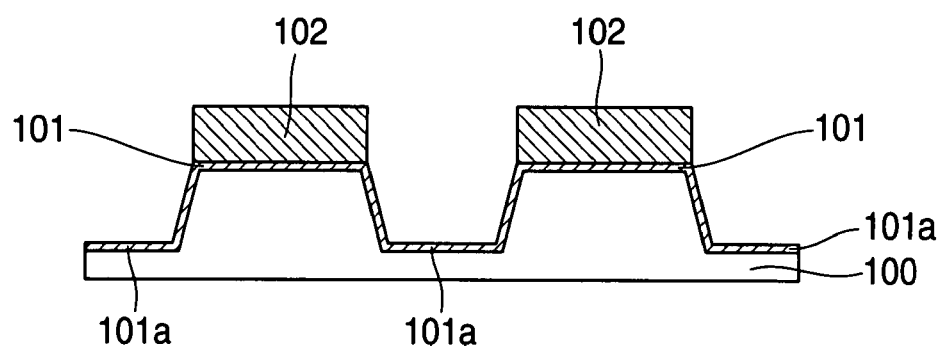
FIG. 3 is a cross-sectional view for illustrating a step (isolating step) in the preparation of a semiconductor sensing FET according to one embodiment (second embodiment) of the invention (first aspect).
Figure 3:
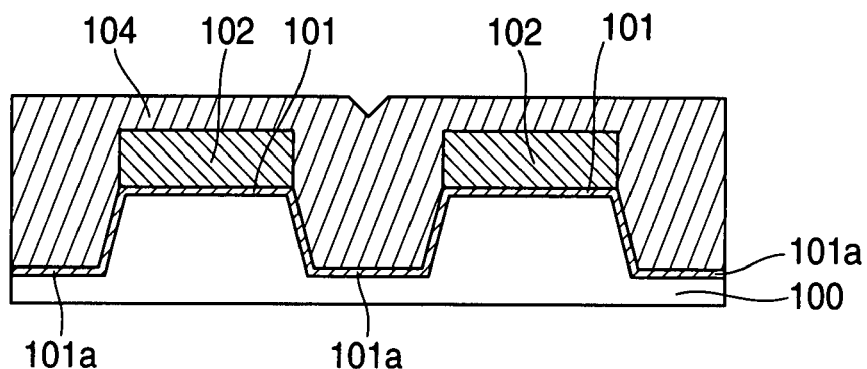
Figure 3:
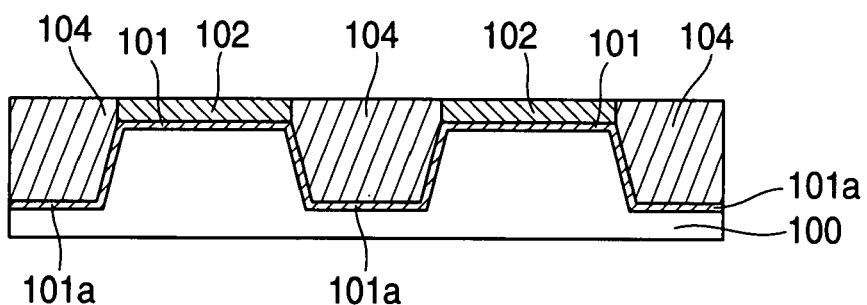
Figure 3:
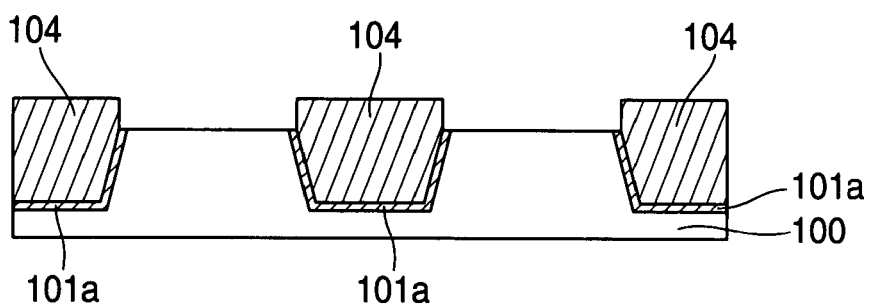
Figure 4:
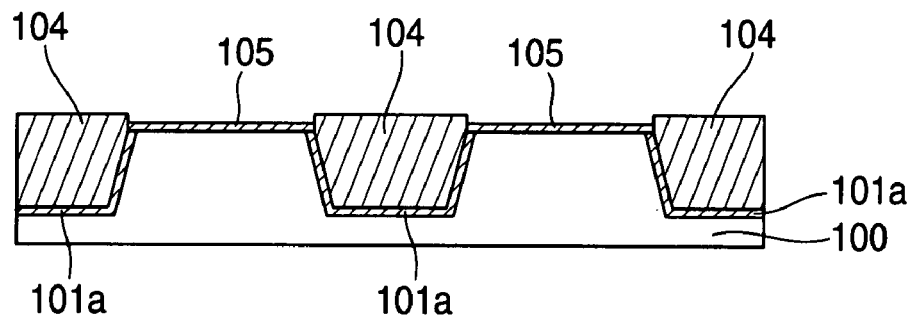
FIG. 4 is a cross-sectional view for illustrating steps (from isolating step to gate forming and extension forming step) in the preparation of a semiconductor sensing FET according to one embodiment (second embodiment) of the invention (first aspect).
Figure 4:
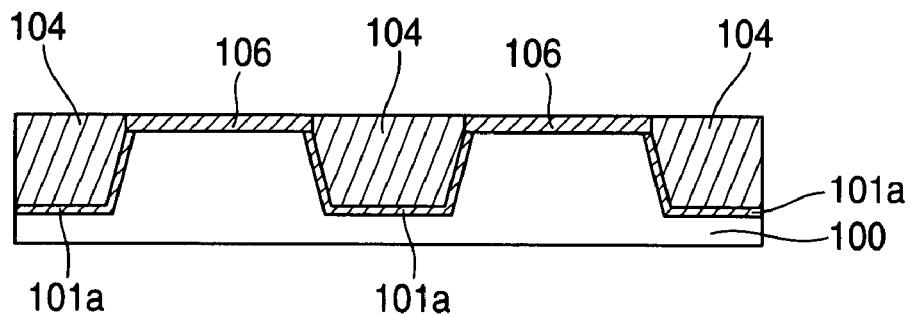
Figure 4:
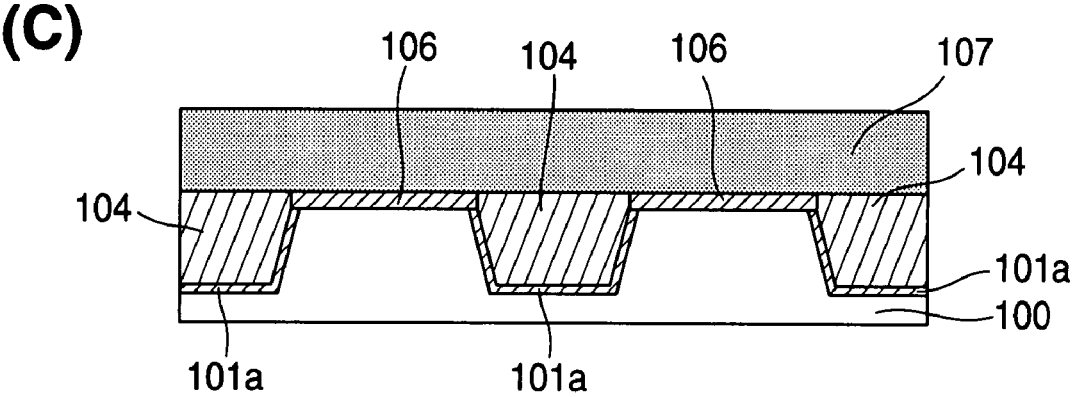
Figure 5:
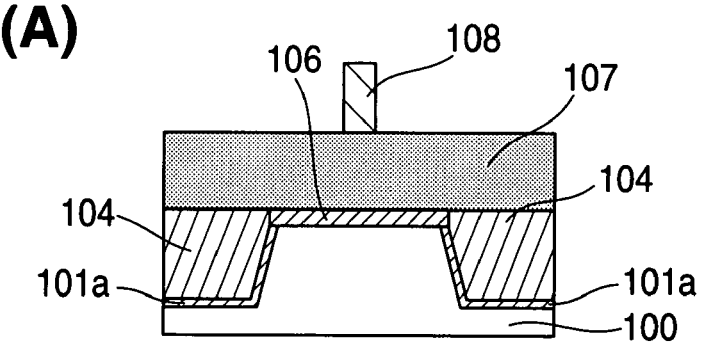
FIG. 5 is a cross-sectional view for illustrating steps (from gate forming and extension forming step to sidewall forming and source/drain forming step) in the preparation of a semiconductor sensing FET according to one embodiment (second embodiment) of the invention (first aspect).
Figure 5:
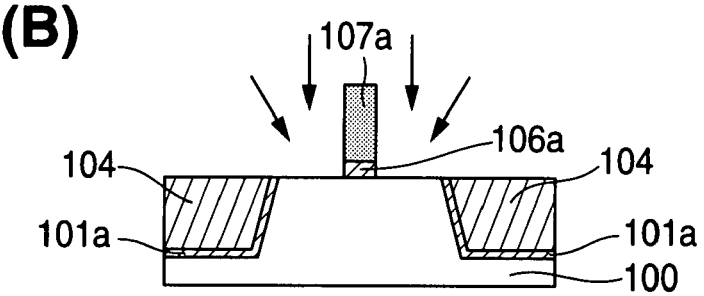
Figure 5:
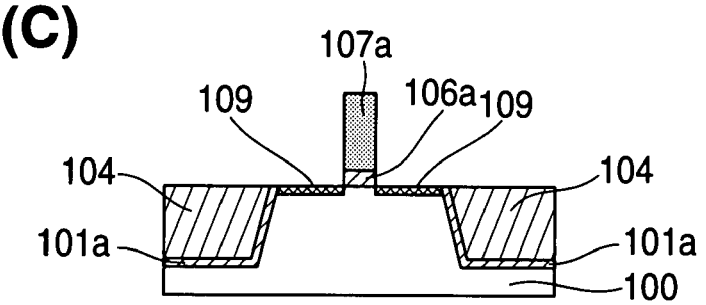
Figure 5:
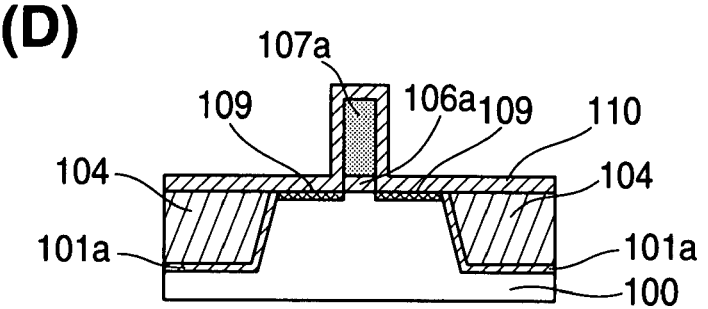
Figure 6:
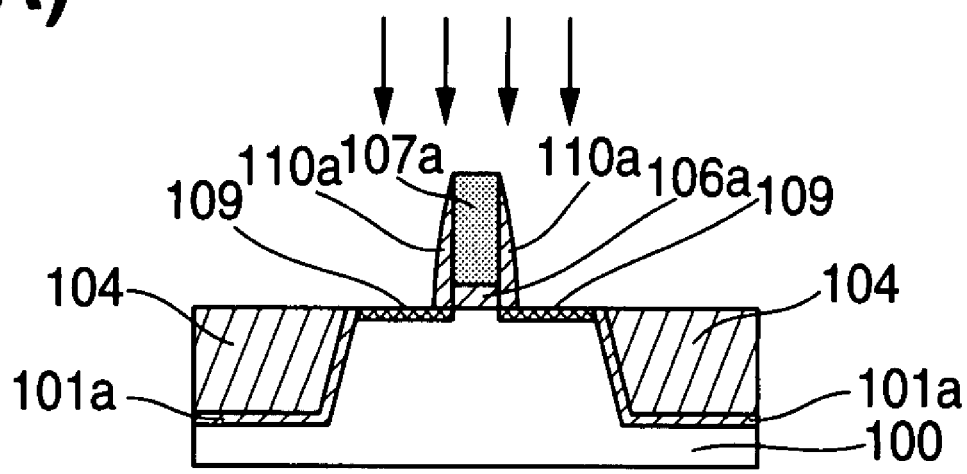
FIG. 6 is a cross-sectional view for illustrating steps (from sidewall forming and source/drain forming step) in the preparation of a semiconductor sensing FET according to one embodiment (second embodiment) of the invention (first aspect).
Figure 6:
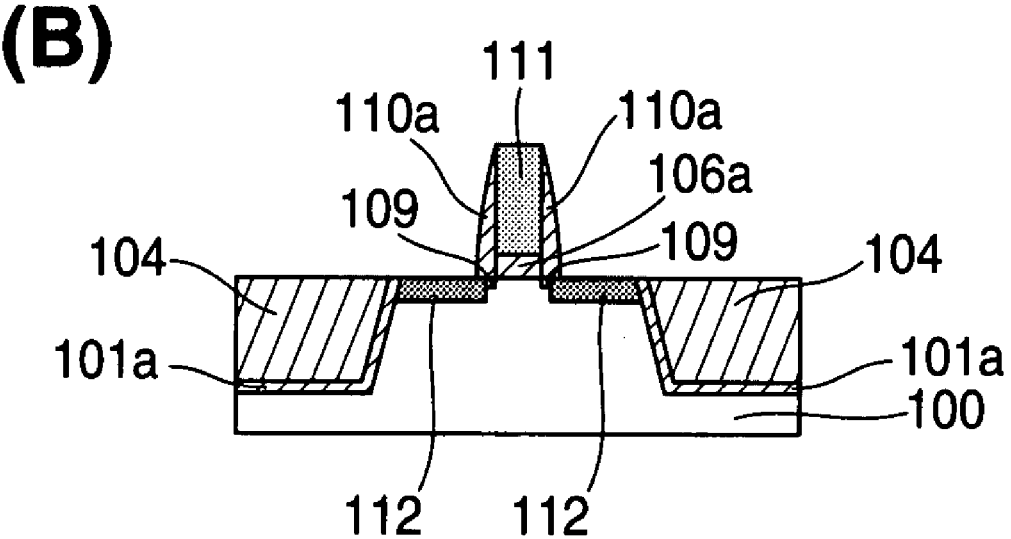
Figure 7:
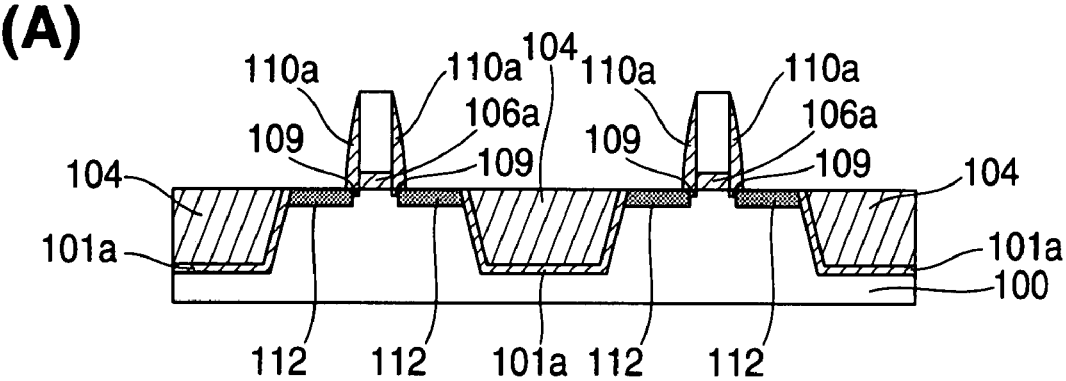
FIG. 7 is a cross-sectional view for illustrating a step (M0 wiring or W plug forming step) in the preparation of a semiconductor sensing FET according to one embodiment (second embodiment) of the invention (first aspect).
Figure 7:
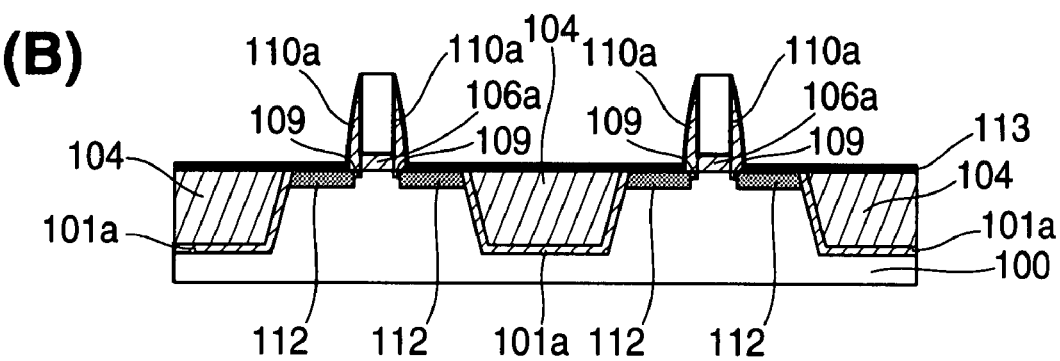
Figure 7:
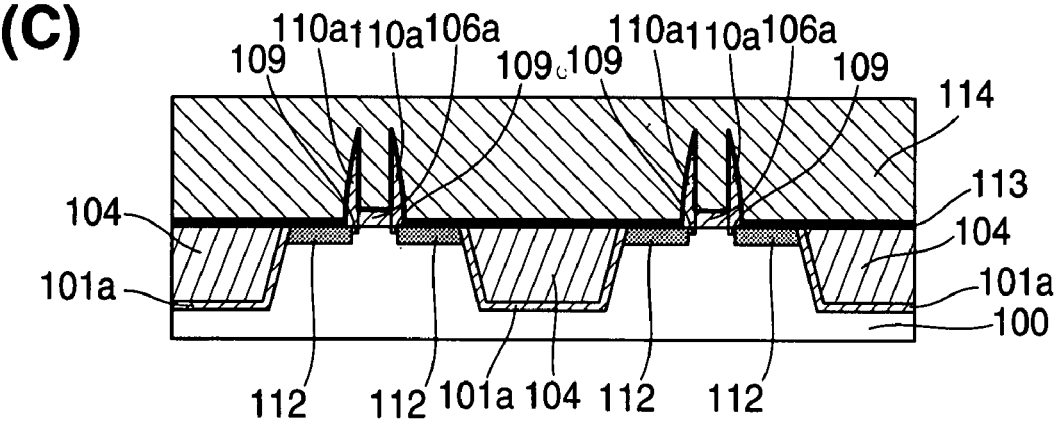
Figure 8:
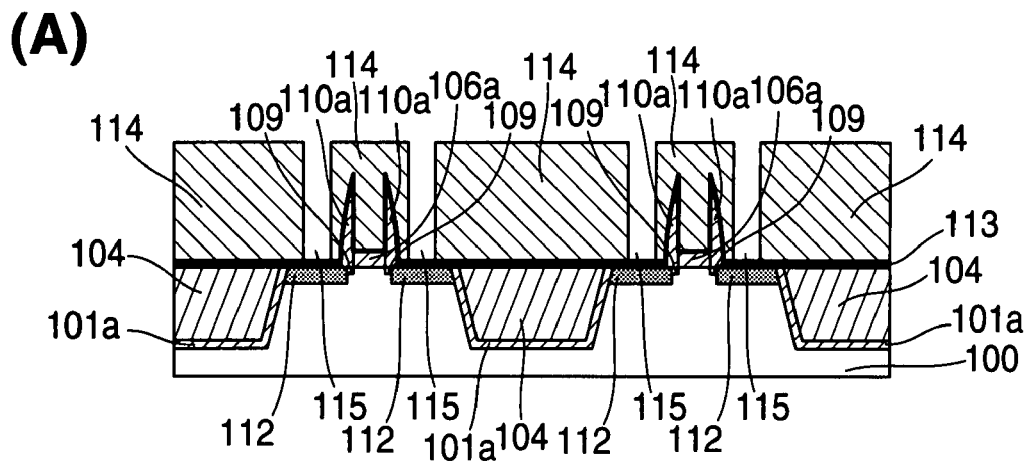
FIG. 8 is a cross-sectional view for illustrating a step (M0 wiring or W plug forming step) in the preparation of a semiconductor sensing FET according to one embodiment (second embodiment) of the invention (first aspect).
Figure 8:
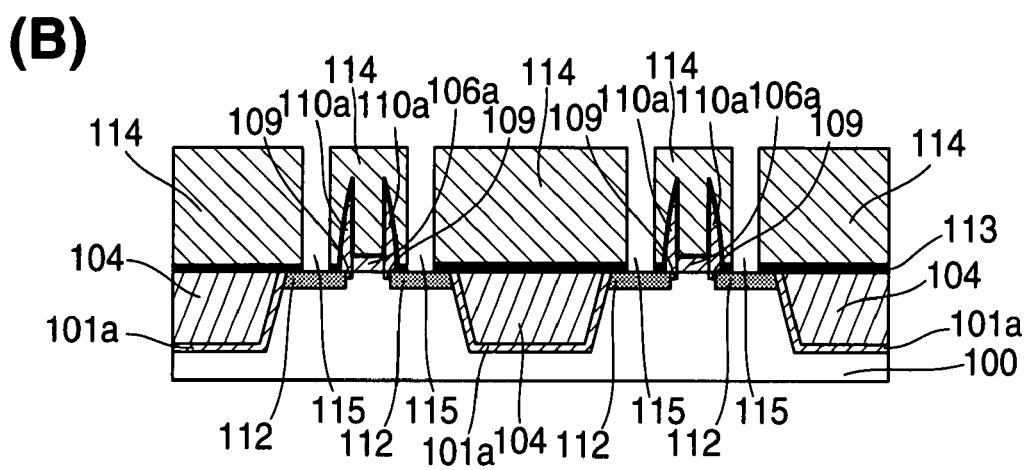
Figure 8:
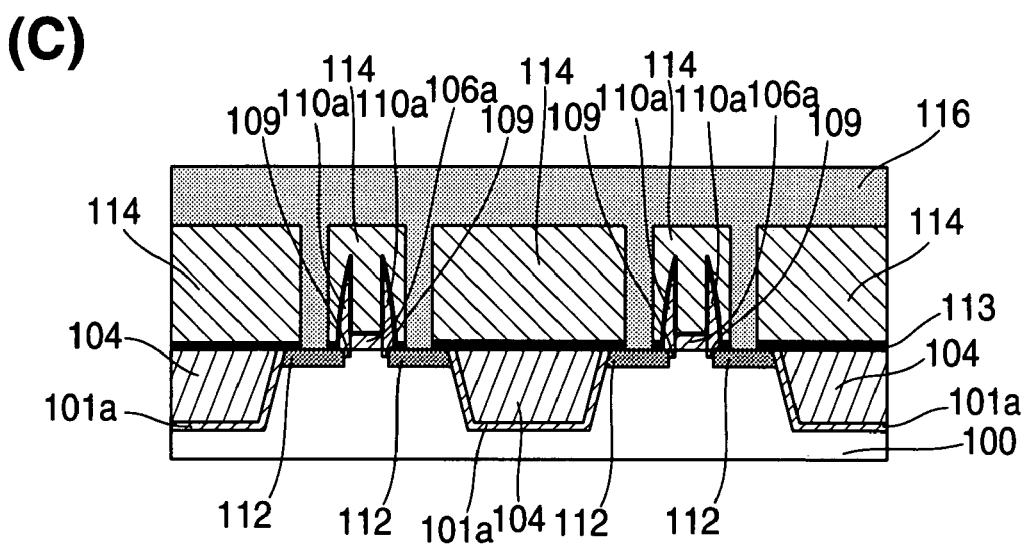
Figure 9:
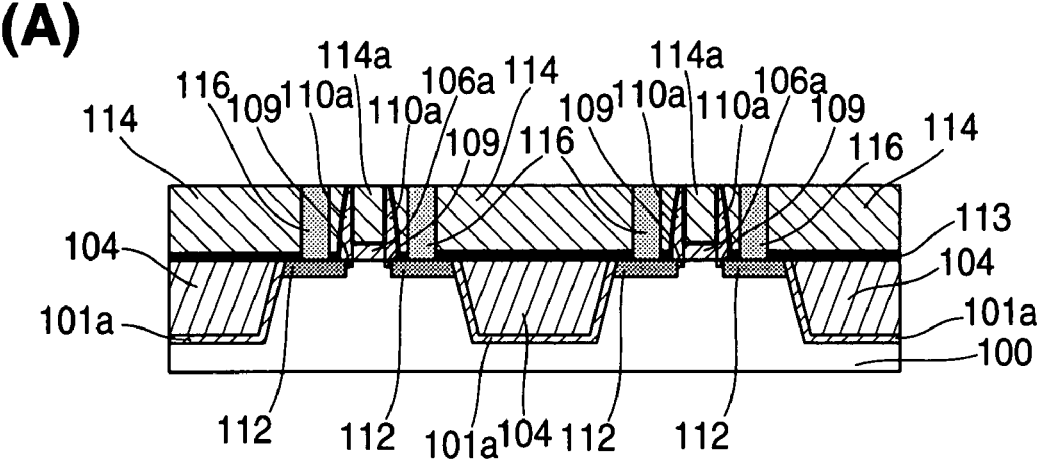
FIG. 9 is a cross-sectional view for illustrating steps (from M0 wiring or W plug forming step to M1 wiring forming step) in the preparation of a semiconductor sensing FET according to one embodiment (second embodiment) of the invention (first aspect).
Figure 9:
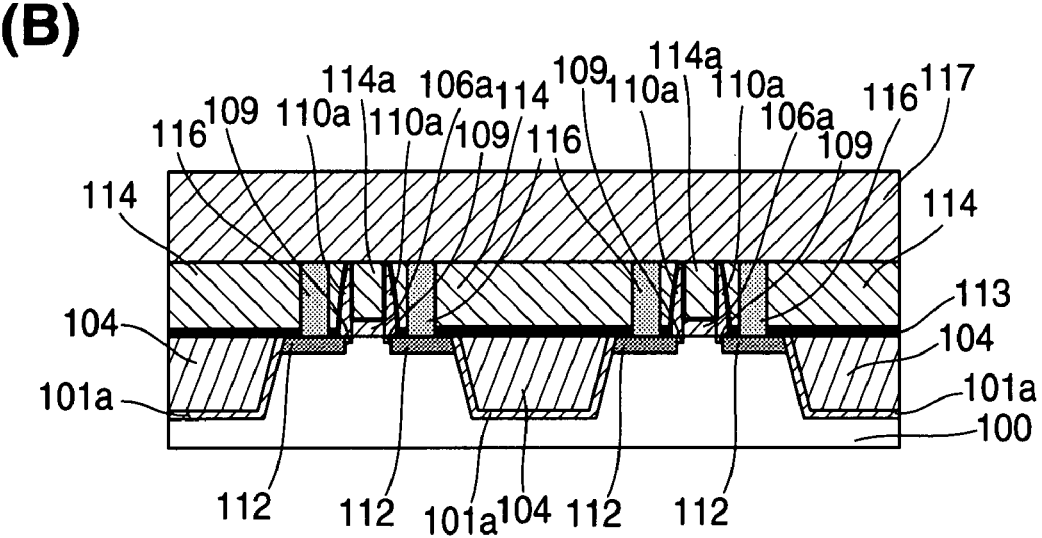
Figure 10:
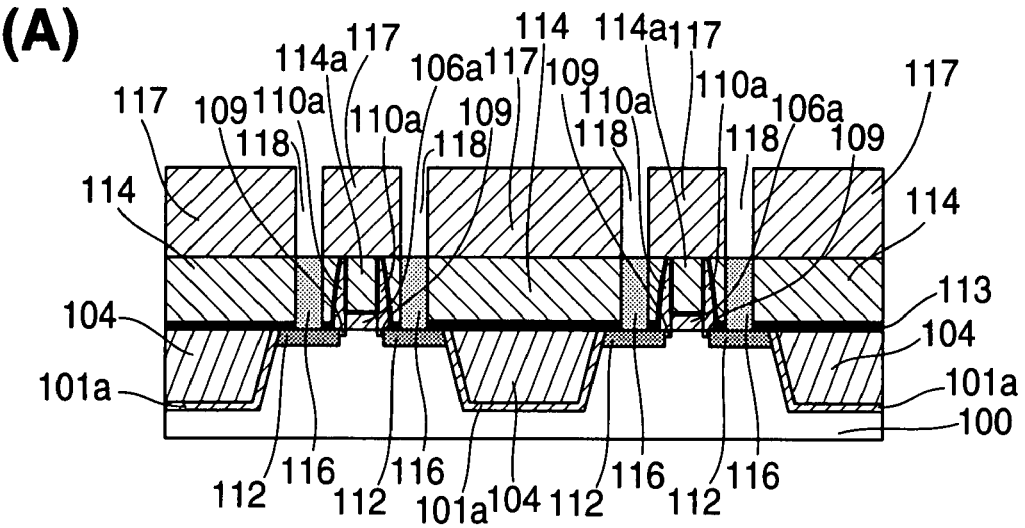
FIG. 10 is a cross-sectional view for illustrating a step (M1 wiring forming step) in the preparation of a semiconductor sensing FET according to one embodiment (second embodiment) of the invention (first aspect).
Figure 10:
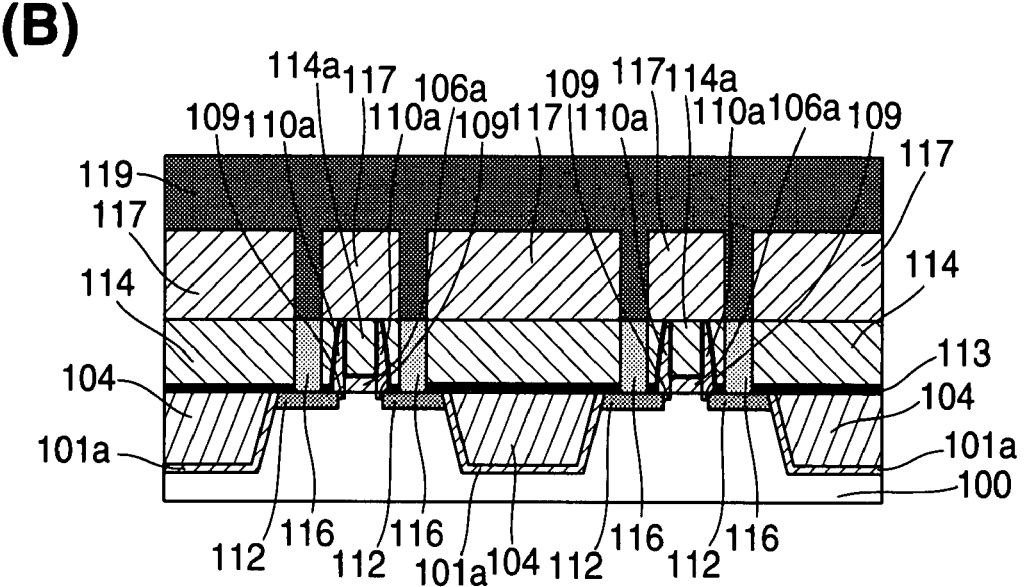
Figure 11:
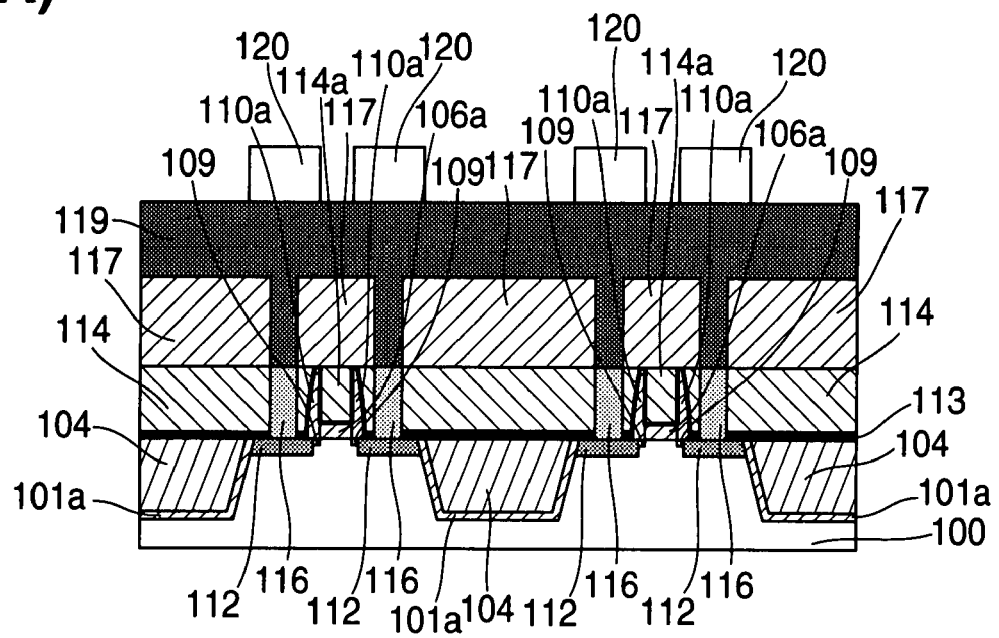
FIG. 11 is a cross-sectional view for illustrating a step (M1 wiring forming step) in the preparation of a semiconductor sensing FET according to one embodiment (second embodiment) of the invention (first aspect).
Figure 11:
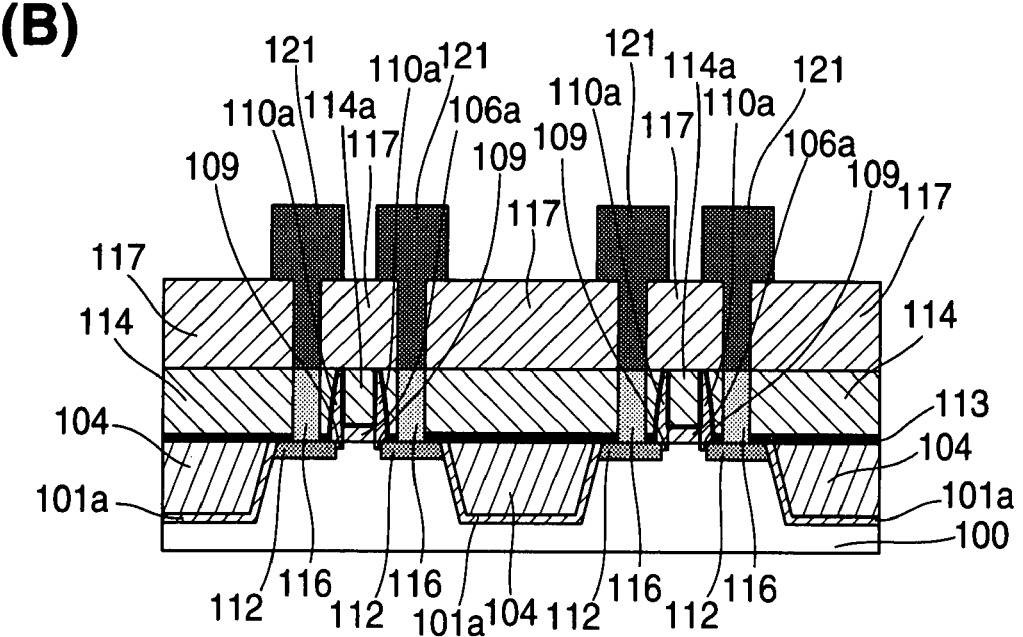
Figure 12:
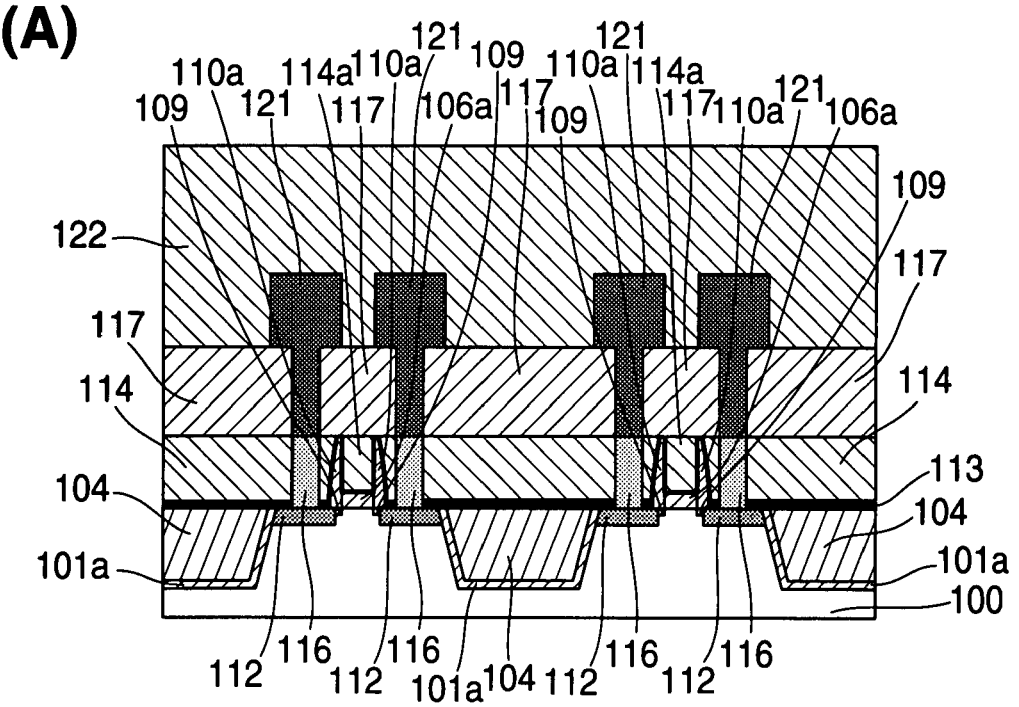
FIG. 12 is a cross-sectional view for illustrating a semiconductor sensing FET according to one embodiment (second embodiment) of the invention (first aspect) and a step (passivation film forming and gate forming step) in the preparation thereof.
Figure 12:
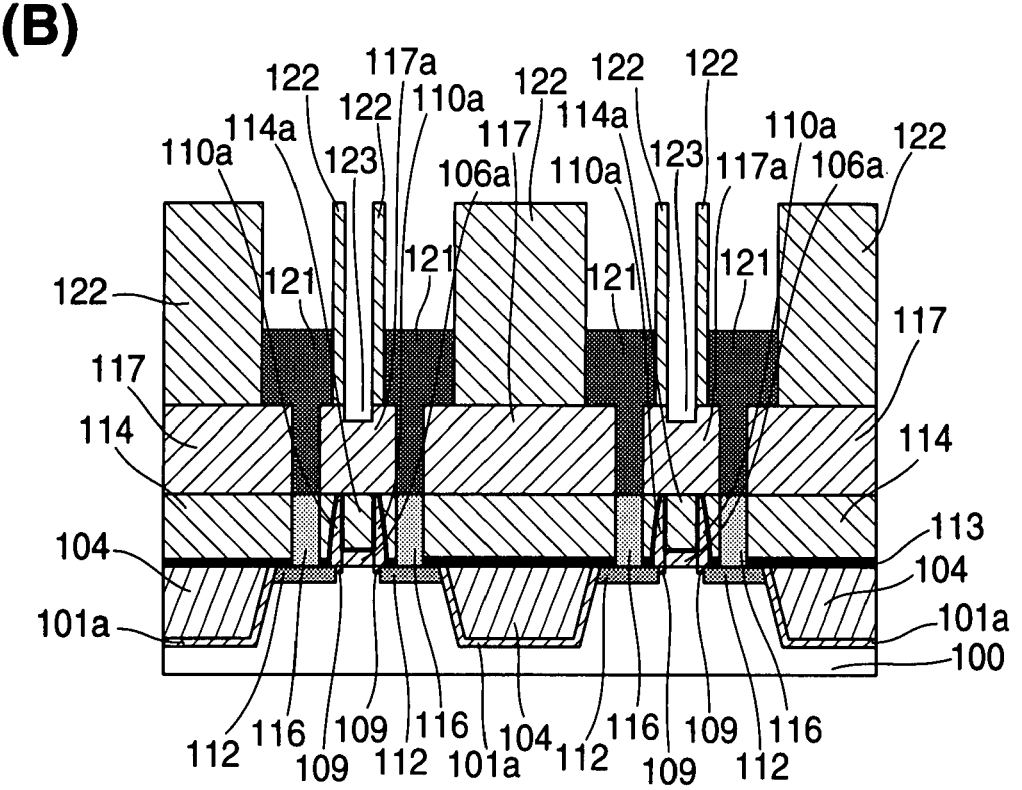

| LEGENDS | |
|---|---|
| 1 | silicon substrate |
| 2 | gate dielectric layer |
| 2a | first silicon oxide layer |
| 2b | silicon nitride layer |
| 2c | second silicon oxide layer |
| 3 | organic monomolecular film |
| 4 | gate electrode |
| 5 | source electrode |
| 6 | drain electrode |
| 7 | channel region |
| 100 | silicon substrate |
| 106a | silicon oxide layer |
| 114 | silicon nitride film (silicon nitride layer) |
| 114a | silicon nitride layer |
| 117a | silicon oxide layer |
| 111a | impurity implanted layer |
| 111b | metal silicide layer |
| 116a | W layer |
| 200 | low-resistance layer |
| K1 | semiconductor sensor chip |

-continued

LEGENDS

| | |
|---|---|
| K11 | board |
| K12 | recess |
| K2 | FET chip |
| K21 | gate dielectric layer |
| K22 | source electrode |
| K220 | source electrode through wiring |
| K23 | drain electrode |
| K230 | drain electrode through wiring |
| K32 | source electrode terminal wiring pattern |
| K320 | source electrode terminal wiring |
| K321 | interconnecting extension from source electrode terminal wiring pattern |
| K33 | drain electrode terminal wiring pattern |
| K330 | drain electrode terminal wiring |
| K331 | interconnecting extension from drain electrode terminal wiring pattern |
| K42 | lead wire (one lead wire) |
| K43 | lead wire (other lead wire) |
| K5 | encapsulant layer |
| K50 | encapsulant |
| K61 | weir layer |
| K62 | rubber layer |
| K63 | lid |
| K7 | measuring instrument |
| K72, K73 | electric signal input/output terminals |
| K8 | anisotropic conductive rubber |
| K91 | reservoir |
| K92 | cavity |

BEST MODE FOR CARRYING OUT THE INVENTION

Now the invention is described in further detail.

First Aspect Invention

The first aspect of the invention is now described.

The first aspect of the invention relates to a semiconductor sensing field effect transistor (FET) comprising a gate dielectric layer formed on silicon, which is to be used as a semiconductor sensing device after an organic monomolecular film is formed on the gate dielectric layer as a direct detector section. The gate dielectric layer has a multilayer structure of silicon oxide layer/silicon nitride layer/silicon oxide layer including, in sequence, a first silicon oxide layer, a silicon nitride layer, and a second silicon oxide layer. It is noted that this multilayer structure may further include between the above-specified layers another layer having a thickness which does not interfere with the function of gate dielectric layer, for example, an etch-stop layer commonly used for the purpose of improving the accuracy of etching during processing of the respective layers.

Such a FET is advantageously used in semiconductor ion sensing and bio-sensing devices. Once an organic monomolecular film, typically an organic silane monomolecular film is formed on the gate dielectric layer on silicon as a direct detector section, the FET can be used as a sensing device. That is, a semiconductor sensing device having an organic monomolecular film/gate dielectric layer/semiconductor structure can be constructed in which an organic monomolecular film is formed as a direct detector section on the gate dielectric layer of the semiconductor sensing FET.

FIG. 1A illustrates one example (first embodiment) of a semiconductor sensing FET according to the first aspect of the invention. FIG. 1B illustrates a semiconductor sensing device which is constructed by forming an organic monomolecular film on the gate dielectric layer of the transistor. Illustrated in FIG. 1 are a silicon substrate 1, a gate dielectric layer 2, an organic monomolecular film 3, a gate electrode 4, a source electrode 5, a drain electrode 6, and channel regions 7. In the first aspect of the invention, gate dielectric layer 2 has a multilayer structure of silicon oxide layer/silicon nitride layer/silicon oxide layer in which a first silicon oxide layer 2a is overlaid with a second silicon oxide layer 2c through an intervening silicon nitride layer 2b as shown in FIG. 1C. Specifically, first silicon oxide layer 2a is contiguous to silicon substrate 1, second silicon oxide layer 2c is exposed outside to present a surface on which an organic monomolecular film serving as a detector section is to be formed, and silicon nitride layer 2b intervenes between first and second silicon oxide layers 2a and 2c so as to block mass transfer, typically of moisture and ions.

By using the FET according to the first aspect of the invention and forming an organic monomolecular film on its gate dielectric layer locally at a site to come in contact with the liquid surface, a semiconductor sensing device can be constructed in which the organic monomolecular film serves as a direct detector section. The semiconductor sensing device operates on the basic principle of detecting as electrical signals changes of surface potential due to ion adsorption, bio-reaction or the like on the surface.

It is noted that the organic monomolecular film may be modified with DNA, enzyme, immunity or the like. It is also possible to use reporter molecules if necessary.

The preferred organic monomolecular film is an organic silane monomolecular film, which can be formed by patterning by a suitable patterning technique.

Using organic silane molecules, an organic silane monomolecular film can be formed on the gate dielectric layer by vapor phase chemical reaction or liquid phase reaction. By optimizing the organic silane monomolecular film, a closest packed film is formed.

The organic silane monomolecular films used herein include monomolecular films of alkoxysilanes having straight hydrocarbon radicals (e.g., alkyl radicals) of 3 to 20 carbon atoms containing at least one amino functional radical ($NH_2$—, —NH—, $C_5H_5N$—, $C_4H_4N$—, etc.) or carboxyl functional radical (—COOH, etc.), and monomolecular films of alkoxysilanes having non-reactive straight alkyl radicals or fluorinated alkyl radicals of 8 to 20 carbon atoms.

The incorporation of reactive functional radicals such as amino and carboxyl functional radicals may be implemented, aside from using alkoxysilanes having such functional radicals, by once forming a monomolecular film using alkoxysilanes having radicals which can be replaced by such functional radicals, for example, amino-inducible radicals such as —Br or —CN, then replacing the amino-inducible radicals by amino radicals.

Of the alkoxysilanes, trialkoxysilanes are preferred for adhesion and other properties, and the preferred alkoxy radicals are alkoxy radicals of 1 to 4 carbon atoms, especially methoxy and ethoxy radicals.

Illustrative examples of the alkoxysilane include $NH_2(CH_2)_3Si(OC_2H_5)_3$, $CH_3(CH_2)_{17}Si(OCH_3)_3$, and $CF_3(CF_2)_7(CH_2)_2Si(OCH_3)_3$.

Now, referring to FIGS. 2 through 12, another embodiment (second embodiment) of the semiconductor sensing FET according to the first aspect of the invention and an appropriate method for the preparation thereof are described. FIG. 12B illustrates one example of the semiconductor sensing FET, which can be prepared by the following method.

Isolation Step

First, an isolated structure is formed. The substrate used herein is a p-type silicon substrate 100. The silicon substrate 100 is placed in a diffusion furnace where it is heated in an oxygen or steam atmosphere to form a silicon oxide film (thermally oxidized film) 101 on the surface of silicon substrate 100 (FIG. 2A). Then heat CVD was performed while introducing silane and argon gases, depositing a silicon nitride ($Si_3N_4$) film 102 (FIG. 2B).

Next, a resist film is formed on silicon nitride film 102 and patterned by lithography, forming a resist pattern 103 at the preselected area (FIG. 2C). The region where resist pattern 103 overlies becomes a device region and the region where resist pattern 103 is absent becomes an isolation region.

Next, by etching through resist pattern 103 as a mask, silicon nitride film 102 and silicon oxide film (thermally oxidized film) 101 are patterned. By further driving the etching, an upper portion of silicon substrate 100 is etched to form a recess (shallow trench) 100a so that portions other than the portions masked by resist pattern 103 are depressed. The side wall of recess (shallow trench) 100a is preferably tapered at an inclination of about 80°.

Next, resist pattern 103 is stripped off, and a silicon oxide film (inner wall oxide film) 101a is formed on the surfaces (side and bottom surfaces) of exposed recess 100a by thermal oxidation (FIG. 3A). The resulting silicon oxide film is contiguous to silicon oxide film (thermally oxidized film) 101 which has not been removed by the above etching.

Next, CVD is performed while introducing silane and argon gases, depositing a silicon oxide film 104 over the entire surface of the substrate (FIG. 3B). By subsequent chemical mechanical polishing (CMP), silicon oxide film 104 is polished away together with an upper portion of silicon nitride film 102 (FIG. 3C). Further, the thus exposed silicon nitride film 102 is etched away together with the underlying silicon oxide film 101 (FIG. 3D). For this etching, wet etching is preferred from the standpoint of selectivity.

Finally, a silicon oxide film (sacrificial oxide film) 105 is formed on the thus exposed surface of silicon substrate 100 (FIG. 4A). It is an oxide film for preventing metal contamination or surface damage during ion implantation. Isolation is completed in this way, achieving shallow trench isolation (STI).

Gate Forming and Extension Forming Steps

Next, by a standard technique or rapid thermal processing (RTP) technique, silicon oxide is deposited on silicon oxide film (sacrificial oxide film) 105, forming a silicon oxide film 106 which is contiguous to silicon oxide film (sacrificial oxide film) 105 and becomes a first silicon oxide layer (FIG. 4B). In order to form silicon oxide film 106 as a thin film, use of the RTP technique is preferred. The use of this technique is crucial in forming miniature devices far below the 100-130 nm node.

Next, by CVD, an aluminum film 107 which serves as a self-alignment mask is deposited over the entire surface of the substrate (FIG. 4C). Further on Al film 107, a resist pattern 108 for forming a gate of the desired size is formed by photolithography (FIG. 5A). The Al film 107, silicon oxide film 106 and an upper portion of silicon oxide film 104 are etched away through resist pattern 108 as a mask, and resist pattern 108 is removed. This yields a layer structure of silicon oxide layer 106a and patterned Al film 107a at the gate region while silicon substrate 100 is exposed again in source/drain-forming regions (FIG. 5B).

Next, a source/drain extension (SD extension) is formed. First, as a p-MOS structure in this case, impurities are implanted into the exposed surface portions of the silicon substrate by ion implantation, specifically extension $BF_2$ implantation and pocket arsenic implantation, forming an impurity-implanted layer 109 (FIG. 5C).

Sidewall Forming and Source/Drain Forming Steps

Next, a dielectric film 110 composed of silicon oxide or silicon nitride is deposited by CVD (FIG. 5D). Subsequent etching-back leaves a sidewall 110a on the side of silicon oxide layer 106a and Al film 107a (FIG. 6A). Then the upper surface of Al film 107a is exposed again. Next, by ion implantation, as a p-MOS structure, boron as p-type impurity is implanted into the exposed surface of the silicon substrate. Since boron is also implanted into Al film 107a, a boron-introduced Al film 111 is formed (FIG. 6B) at the same time as an impurity-implanted layer 112 is formed. After the ion implantation, diffusion (impurity activation) is caused by heat treatment, forming source and drain regions. The above extension $BF_2$ implantation and pocket arsenic implantation is generally referred to as "shallow junction" whereas this source/drain formation is referred to as "deep junction."

M0 Wiring (W Plug) Forming Step

Next, M0 wiring or tungsten plug is formed. First, boron-introduced Al film 111 serving as a self-alignment mask is removed by wet etching (FIG. 7A).

Then, contact holes are formed by depositing an etch-stop layer 113 composed of silicon nitride, for example, on the entire surface of the substrate (FIG. 7B), and overlaying it with a silicon nitride film (interlayer dielectric) 114 (FIG. 7C). During the process, the cavity defined as a result of boron-introduced Al film 111 being removed is filled with silicon nitride. It is noted that when silicon nitride is used as etch-stop layer 113, silicon nitride film (interlayer dielectric) 114 is integral with etch-stop layer 113 to form a common silicon nitride layer.

Next, the surface of silicon nitride film (interlayer dielectric) 114 is flattened by a CMP process, after which contact holes 115 for source and drain are formed by a photolithography process (FIG. 8A). It is noted that although etch-stop layer 113 is not necessarily needed, the provision of etch-stop layer 113 is preferred from the standpoint of preventing over-etching in the preselected regions.

Next, etch-stop layer 113 at the bottom of contact holes 115 is etched away, whereby the surface of impurity-implanted layer 112 is exposed within contact holes 115 (FIG. 8B). Next, a titanium barrier metal layer is formed on the inner surface of contact holes 115, after which contact holes 115 are filled with tungsten (W) by metal CVD, and a tungsten film 116 is formed over the entire substrate surface (FIG. 8C). Then the structure is polished down by a CMP process until the top edges of sidewalls 110 are removed, forming M0 wiring or W plugs (FIG. 9A). As a result, the upper surface of silicon nitride layer 114a with which the cavity left after removal of the boron-introduced Al film 111 is filled is exposed.

M1 Wiring Forming Step

Next, a silicon oxide ($SiO_2$) film 117 is formed over the entire substrate surface by a CVD process using p-TEOS (FIG. 9B); contact holes 118 are formed by a photolithography process (FIG. 10A); contact holes 118 are filled with aluminum by CVD, and an aluminum film 119 is formed over the entire substrate surface by sputtering (FIG. 10B).

Next, on Al film 119 above contact holes 118, a resist pattern 120 is formed for processing Al film 119 into a wiring pattern (FIG. 11A). The Al film 119 is patterned by a photolithography process, and resist pattern 120 is removed, forming a M1 wiring or Al wiring 121 (FIG. 11B).

Passivation Film Forming and Gate Forming Steps

Finally, a passivation film (silicon nitride film) 122 is formed over the entire substrate surface so as to cover Al wiring 121 (FIG. 12A). By a photolithography process, the Al wiring is exposed, and those portions of silicon oxide ($SiO_2$)

film 117 which are disposed above silicon nitride layer 114a are exposed (so that an upper portion of silicon oxide (SiO₂) film 117 is depressed in the illustrated example). A gate 123 is formed where silicon oxide film 117a on silicon nitride layer 114a serves as a second silicon oxide layer (FIG. 12B).

By the overall procedure described above, the semiconductor sensing FET can be produced. In the illustrated embodiment, silicon oxide layer 106a as the first silicon oxide layer, silicon nitride layer 114a as the silicon nitride layer, and silicon oxide layer 117a as the second silicon oxide layer lie in sequence on silicon substrate 100, thereby constructing a gate dielectric layer having a multilayer structure of silicon oxide layer/silicon nitride layer/silicon oxide layer. If an organic monomolecular film is then formed on silicon oxide layer 117a of gate 123, a semiconductor sensing device is obtained.

The semiconductor sensing FET according to the first aspect of the invention includes a preferred embodiment in which a low resistance layer is buried in the gate dielectric layer. Exemplary is a structure in which an internal part of the layer structure including in sequence a first silicon oxide layer, a silicon nitride layer, and a second silicon oxide layer, especially part of the silicon nitride layer is replaced by a low-resistance layer.

Figure 13:
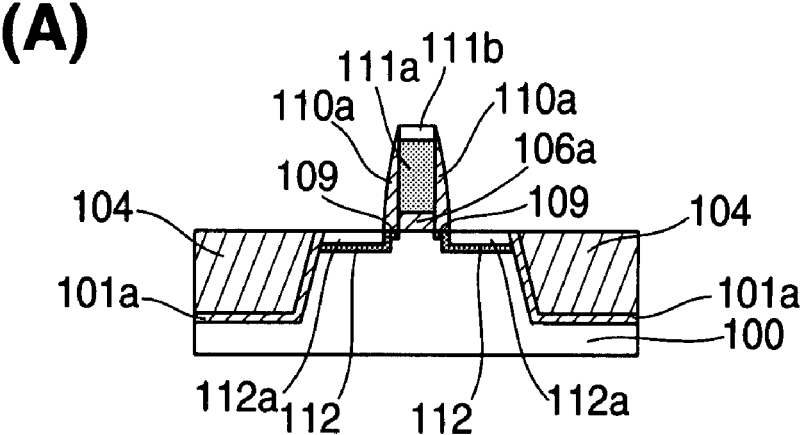
FIG. 13 is a cross-sectional view for illustrating steps (from silicidation step to M0 wiring or W plug forming step) in the preparation of a semiconductor sensing FET according to one embodiment (third embodiment) of the invention (first aspect).
Figure 13:
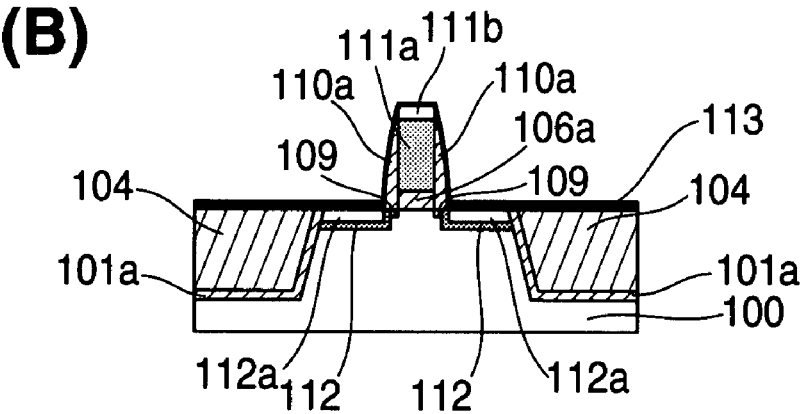
Figure 13:
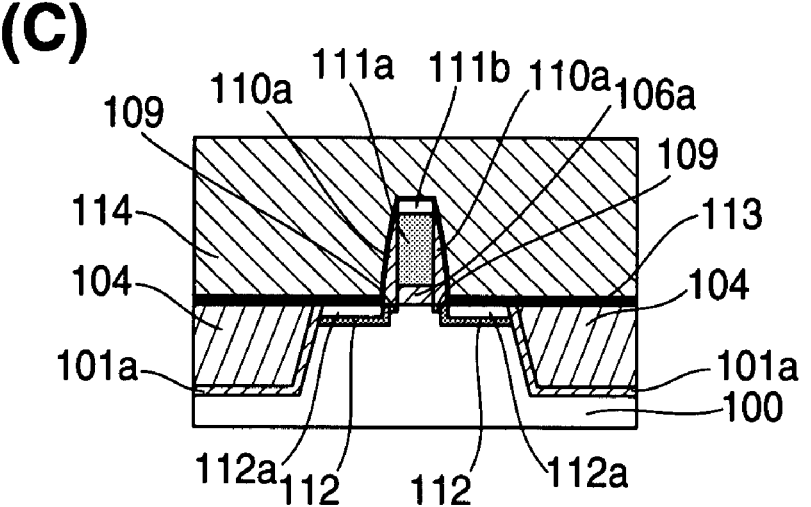
Figure 14:
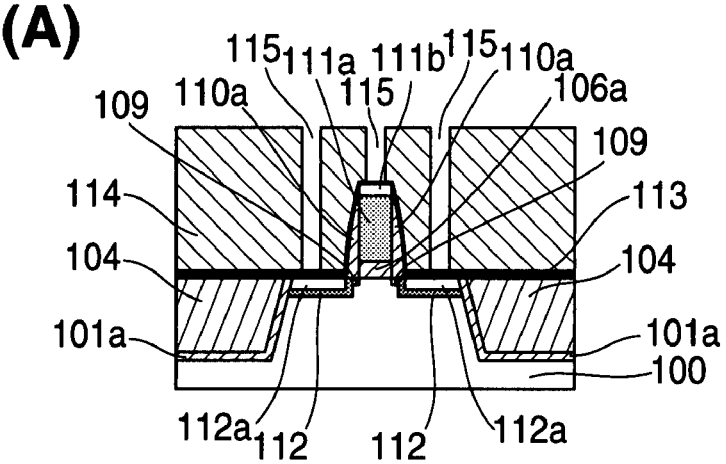
FIG. 14 is a cross-sectional view for illustrating a step (M0 wiring or W plug forming step) in the preparation of a semiconductor sensing FET according to one embodiment (third embodiment) of the invention (first aspect).
Figure 14:
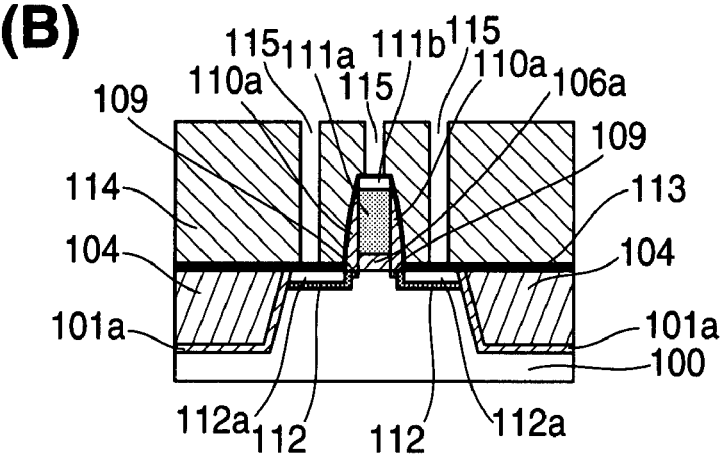
Figure 14:
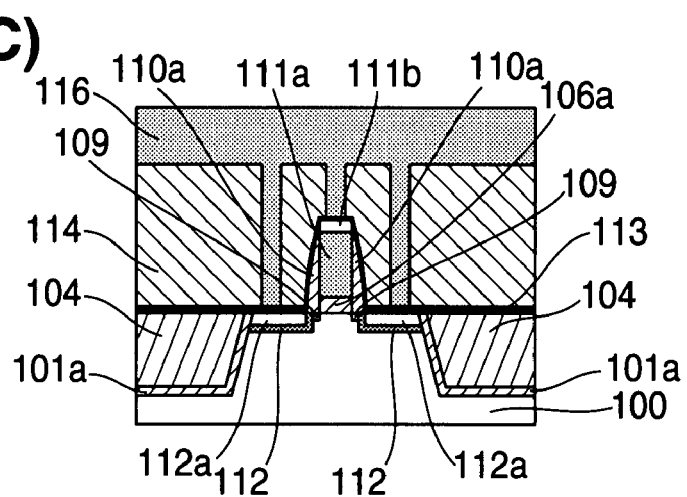
Figure 15:
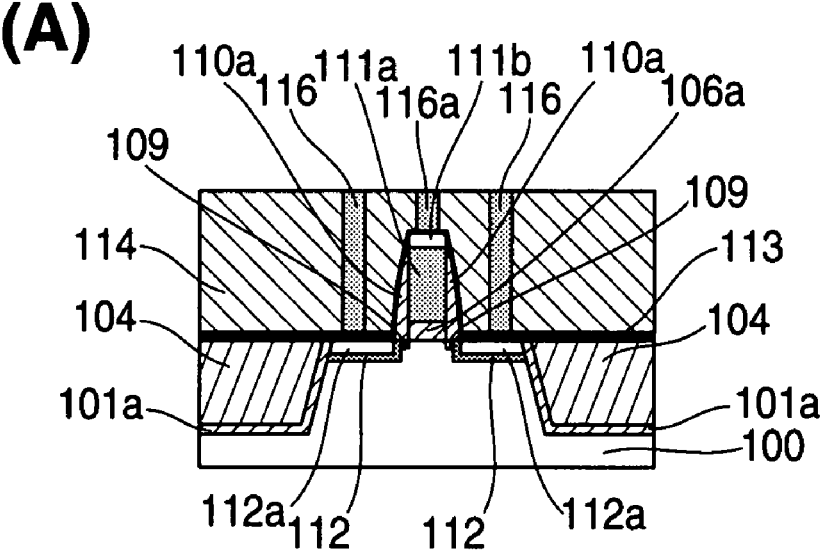
FIG. 15 is a cross-sectional view for illustrating a semiconductor sensing FET according to one embodiment (third embodiment) of the invention (first aspect) and a step (M0 wiring or W plug forming step) in the preparation thereof.
Figure 15:
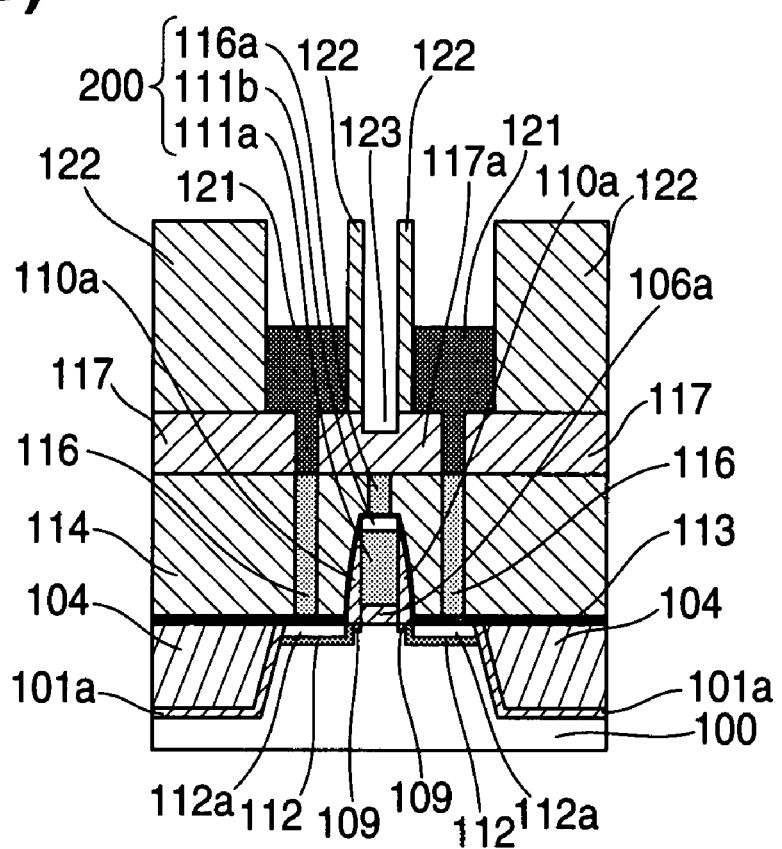

Referring to FIGS. 13 to 15, the semiconductor sensing FET having a low resistance layer incorporated therein (third embodiment) and a preferred method of production are described. FIG. 15B illustrates one exemplary semiconductor sensing FET having a low resistance layer incorporated therein. In this semiconductor sensing FET, a low resistance layer 200 is formed that extends through silicon nitride film (interlayer dielectric) 114 serving as the intervening silicon nitride layer between silicon oxide layer 106a serving as the first silicon oxide layer and silicon oxide layer 117a serving as the second silicon oxide layer and is contiguous to silicon oxide layer 106a and silicon oxide layer 117a. In this embodiment, low resistance layer 200 has a structure including an impurity-implanted layer (boron-implanted film) 111a, a metal silicide layer 111b, and a tungsten layer 116a disposed in sequence from the side of silicon oxide layer 106a upward. The semiconductor sensing FET of this structure can be produced by the following method.

Each of the isolation step, gate forming and extension forming step, and sidewall forming and source/drain forming step may be the same as in the second embodiment illustrated above in conjunction with FIG. 2A to FIG. 6B. Specifically, the aluminum film formed in the second embodiment may be replaced by a polycrystalline silicon (polysilicon), and in this case, impurity-implanted layer 112 is formed by boron ion implantation and a boron-implanted silicon film 111a is formed in place of the boron-implanted aluminum film.

In this embodiment, subsequent to the source/drain forming step, a silicidation step and a M0 wiring forming step are sequentially conducted.

Silicidation Step

The silicidation step is carried out in order to reduce the resistance of the boron-implanted source, drain and gate and further to accelerate signal detection. Here a metal thin film is first deposited on the entire surface of the substrate by sputtering, followed by heat treatment whereby an upper portion of impurity-implanted layer (boron-implanted silicon film) 111a is silicided into a metal silicide layer 111b, and an upper portion of impurity-implanted layer 112 is silicided into a metal silicide layer 112a (FIG. 13A). It is noted that the metal thin film which has not contributed to silicidation is removed by selective wet etching. Suitable materials of which the metal thin film can be made include Co, Ni, and Pt, from which cobalt silicide, nickel silicide, and platinum silicide are formed, respectively.

M0 Wiring (W Plug) Forming Step

Next, M0 wiring or W plugs are formed. First, contact holes are formed by depositing an etch-stop layer 113 composed of silicon nitride, for example, on the entire substrate surface (FIG. 13B), and overlaying it with a silicon nitride film (interlayer dielectric) 114 (FIG. 13C).

Next, the surface of silicon nitride film (interlayer dielectric) 114 is flattened by a CMP process, after which contact holes 115 are formed above the source, drain and gate by a photolithography process (FIG. 14A). It is noted that although etch-stop layer 113 is not necessarily needed, the provision of etch-stop layer 113 is preferred from the standpoint of preventing over-etching in the preselected regions.

Next, etch-stop layer 113 at the bottom of contact holes 115 is etched away, whereby metal silicide layers 111b and 112a are exposed within contact holes 115 (FIG. 14B). Next, a Ti/TiN barrier metal layer is formed on the inner surface of contact holes 115, after which contact holes 115 are filled with tungsten (W) by metal CVD, and a tungsten film 116 is formed over the entire substrate surface (FIG. 14C). Then the structure is polished down by a CMP process until tungsten film 116 on silicon nitride film 114 is removed, forming a M0 wiring or W plugs (FIG. 15A).

The procedure subsequent to the M0 wiring forming step may be the same as in the second embodiment. By way of the M1 wiring forming step and passivation film and gate forming step, a semiconductor sensing FET can be produced. In FIGS. 13 to 15, those parts formed by the same steps as in the second embodiment are designated by like numerals and their description is omitted.

In this embodiment, silicon oxide layer 106a as the first silicon oxide layer, silicon nitride film 114 as the silicon nitride layer, and silicon oxide layer 117a as the second silicon oxide layer are deposited in sequence on silicon substrate 100; part of silicon nitride film 114 is replaced by low resistance layer 200 including impurity-implanted layer 111a, metal silicide layer 111b and tungsten layer 116a laminated in sequence; and a gate dielectric layer in which this low resistance layer 200 is buried within the multilayer structure of silicon oxide layer/silicon nitride layer/silicon oxide layer is formed. If an organic monomolecular film is then formed on silicon oxide layer 117a of gate 123, a semiconductor sensing device may be constructed.

It is possible to use an n-type silicon substrate instead of the p-type silicon substrate. In this embodiment, for formation of source/drain extension (SD extension), as an n-MOS structure, an impurity-introduced layer 109 may be formed by introducing impurities into the exposed surface portion of the silicon substrate by ion implantation, specifically by extension arsenic implantation, and pocket BF₂ implantation or pocket iridium implantation, and an impurity-implanted layer 112 may be formed by implanting arsenic as n-type impurity into n-MOS (exposed surface portion of silicon substrate).

Figure 16:
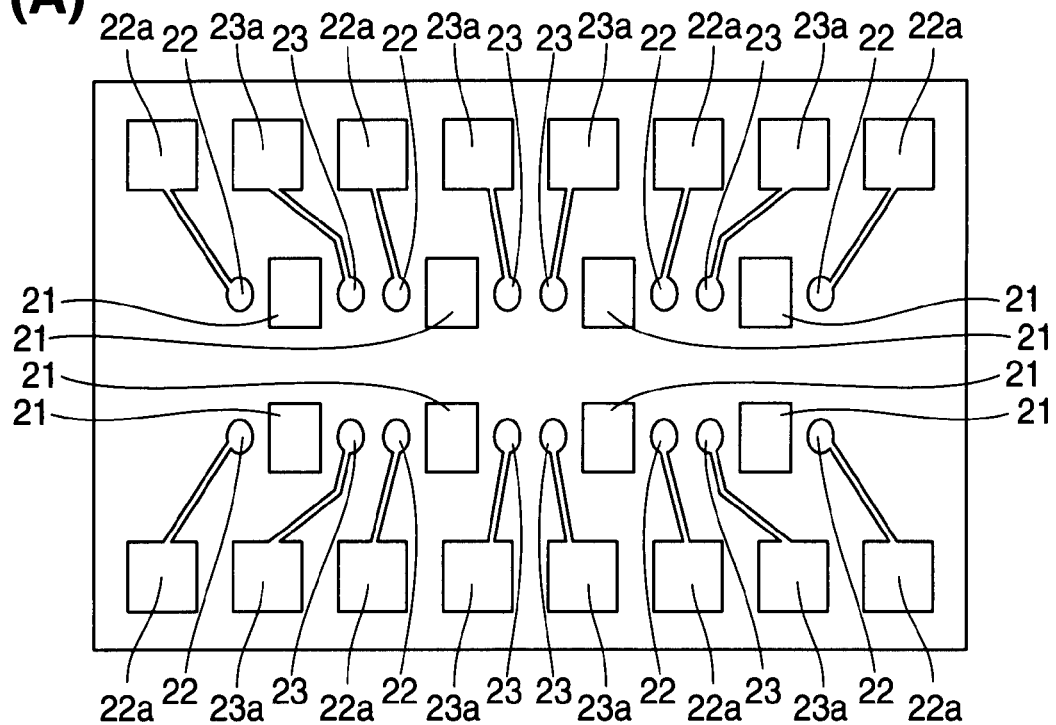
FIG. 16 is a schematic view illustrating a plurality of semiconductor sensing FETs formed on a substrate according to the invention (first aspect).
Figure 16:
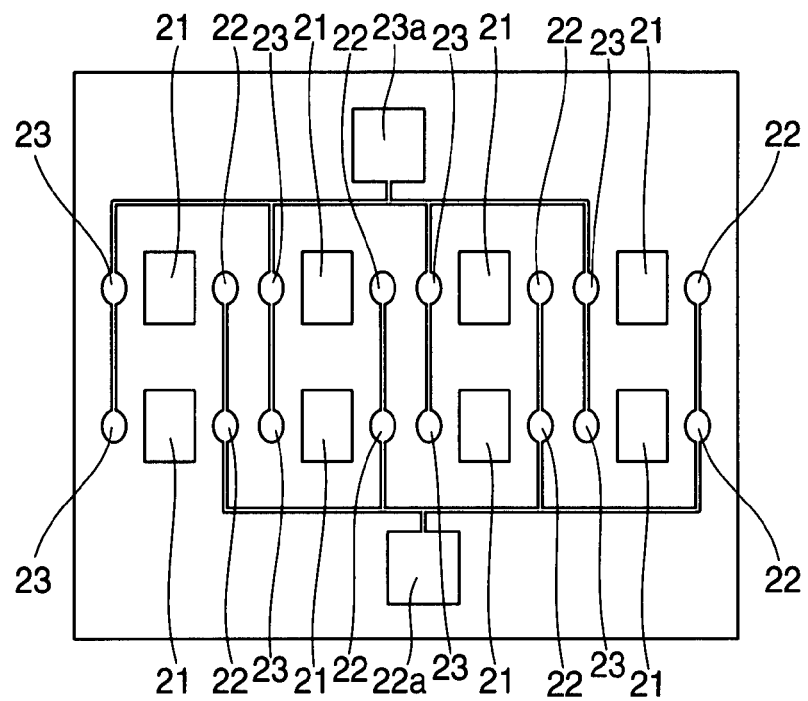
Figure 17:
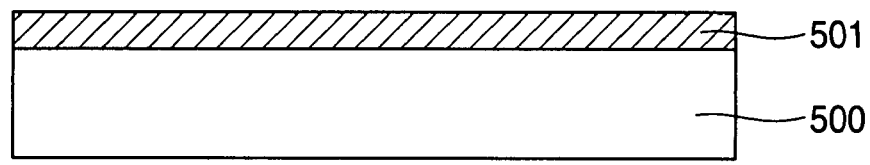
FIG. 17 is a cross-sectional view for illustrating steps for the preparation of a prior art semiconductor sensing FET.
Figure 17:
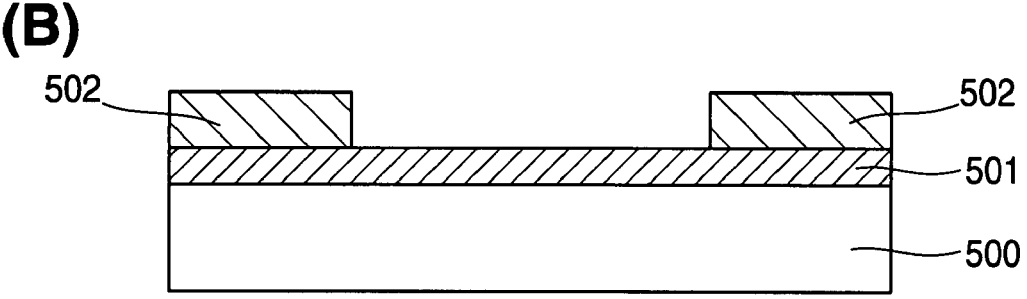
Figure 17:
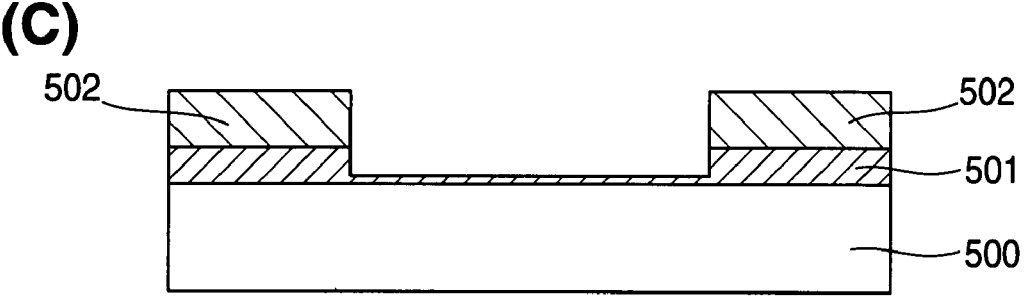
Figure 17:
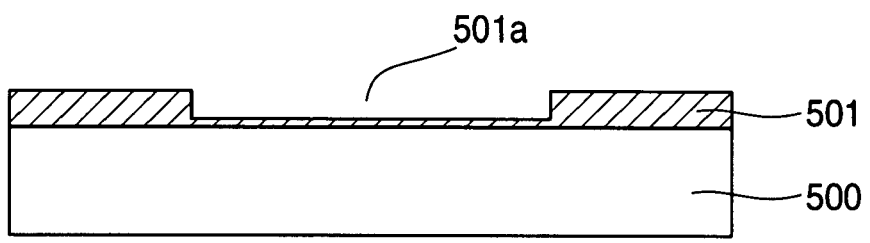
Figure 18:
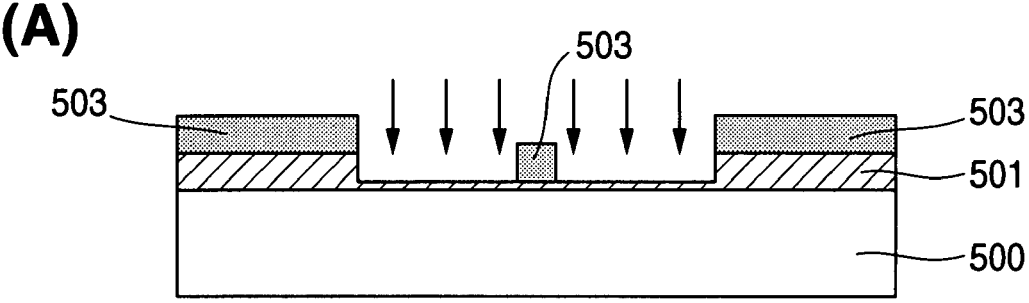
FIG. 18 is a cross-sectional view for illustrating steps for the preparation of a prior art semiconductor sensing FET.
Figure 18:
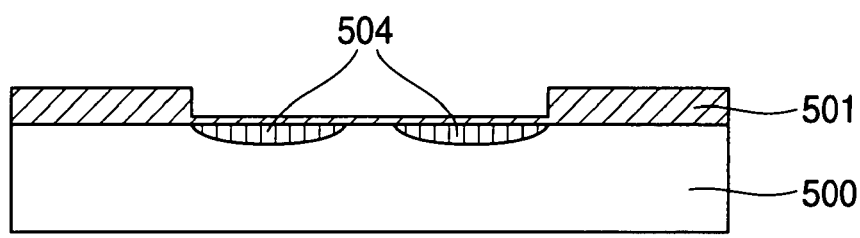
Figure 18:
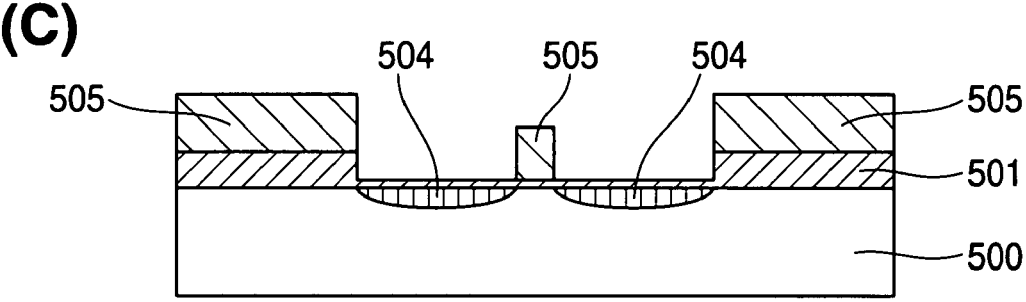
Figure 18:
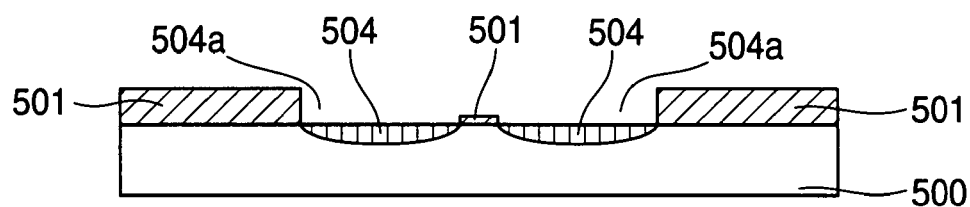
Figure 19:
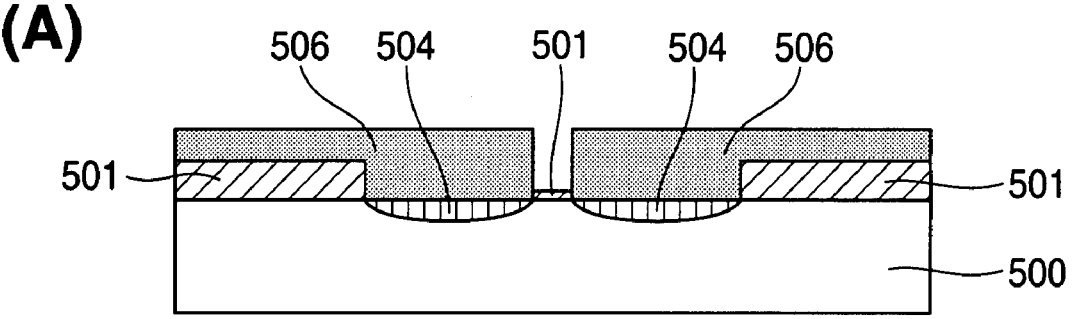
FIG. 19 is a cross-sectional view for illustrating steps for the preparation of a prior art semiconductor sensing FET.
Figure 19:
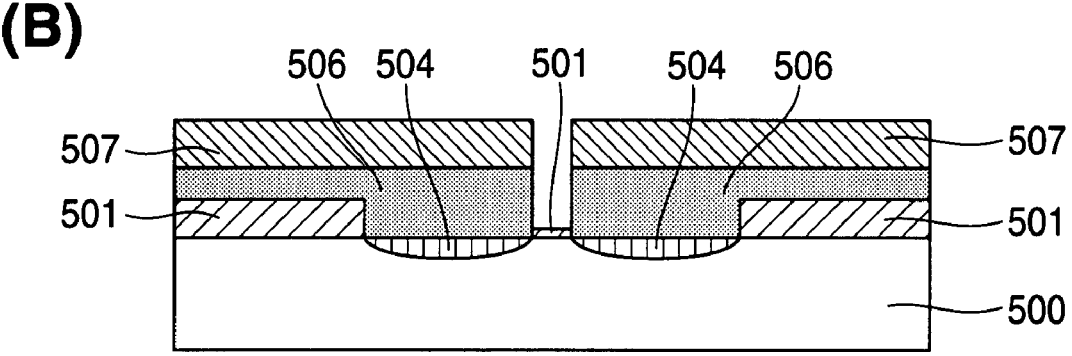
Figure 19:
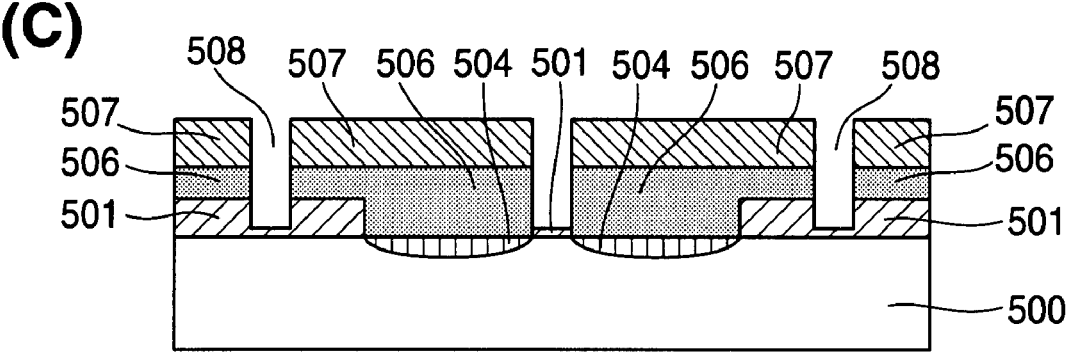

Further, as shown in FIGS. 16A and 16B, by providing a plurality of the above-described FET structures on a silicon substrate, a device capable of plural sensing operations at the same time can be constructed. In this case, it is possible that each sensor section (gate, source and drain) is provided with source and drain electrodes as shown in FIG. 16A, and that a source electrode and a drain electrode are made common to sensor sections for integration as shown in FIG. 16B. The substrate may be either a p-type silicon substrate or a n-type silicon substrate, and a c-MOS having alternately arranged p-MOS and n-MOS is also possible. Illustrated in FIG. 16 are gates 21, sources 22, source electrodes 22a, drains 23, and drain electrodes 23a.

Second Aspect Invention

Described below is the second aspect of the invention.

The second aspect of the invention relates to a semiconductor sensor chip comprising a FET chip having a gate dielectric layer, a source electrode, and a drain electrode integrated on a silicon substrate, a source electrode terminal wiring connected to the source electrode, and a drain electrode terminal wiring connected to the drain electrode. The FET chip, the source electrode terminal wiring, and the drain electrode terminal wiring are sealed with an encapsulant or with a board on which the FET chip, the source electrode terminal wiring, and the drain electrode terminal wiring are disposed and an encapsulant, such that the gate dielectric layer of the FET chip, an end portion of the source electrode terminal wiring which is not connected to the source electrode, and an end portion of the drain electrode terminal wiring which is not connected to the drain electrode are exposed.

Figure 20:
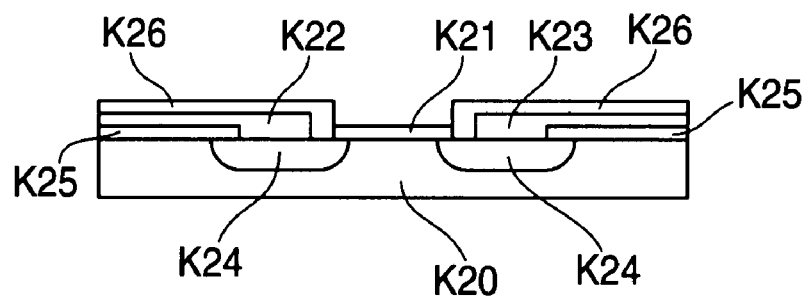
FIG. 20 illustrates a FET and a semiconductor sensing system comprising the same, FIG. 20A being a cross-sectional view of the FET and FIG. 20B being a schematic view showing the arrangement of the semiconductor sensing system using the FET.
Figure 20:
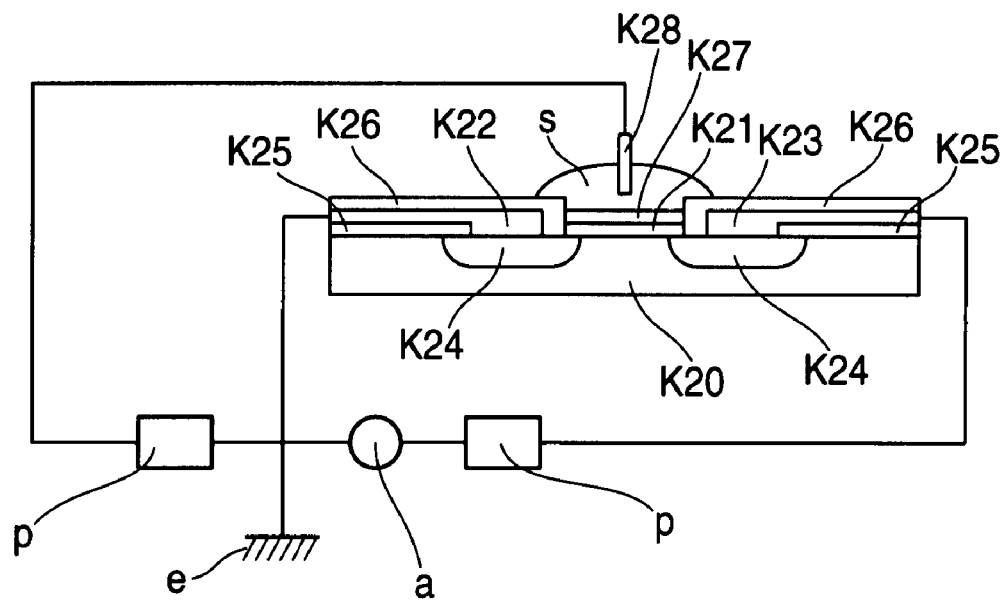
Figure 21:
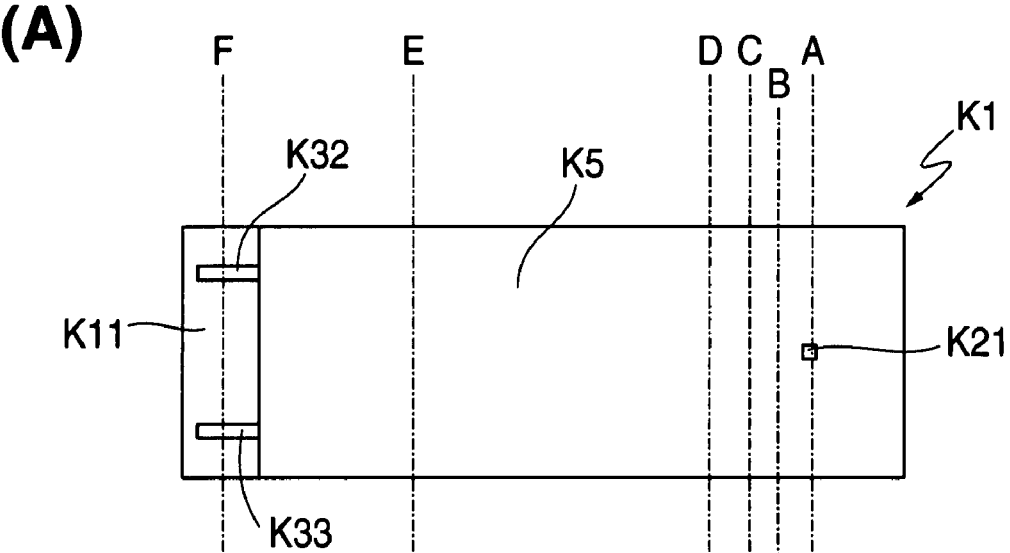
FIG. 21 illustrates one example in a first embodiment of the semiconductor sensor chip according to the invention (second aspect), FIG. 21A being a plan view, FIG. 21B being a side elevation, and FIG. 21C being a plan view of the state prior to sealing with an encapsulant layer (or with the encapsulant layer removed).
Figure 21:
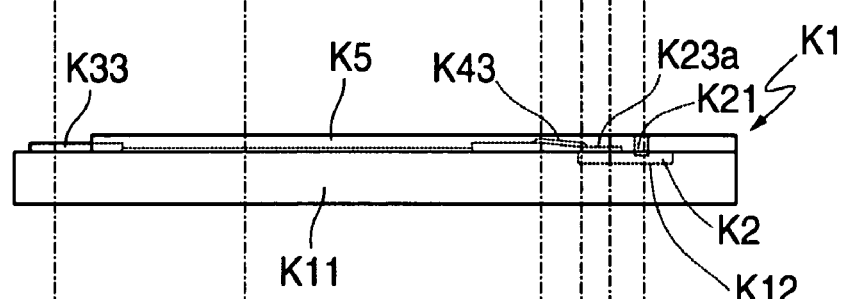
Figure 21:
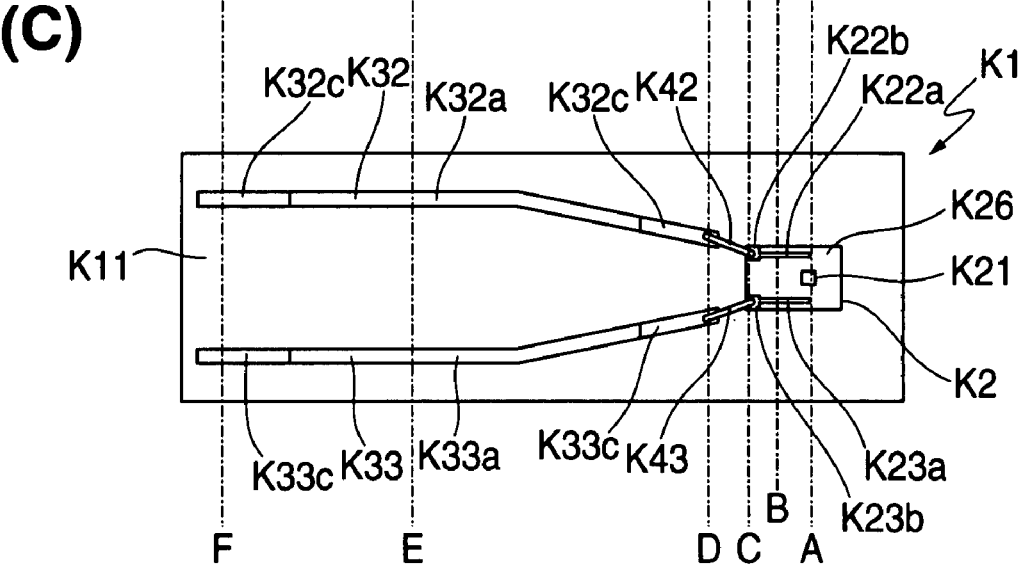
Figure 22:
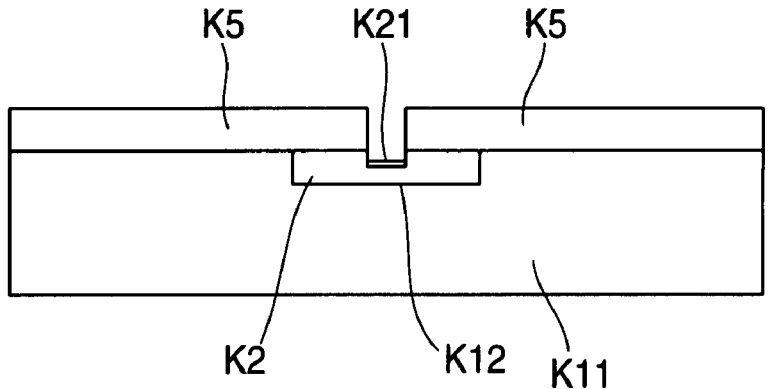
FIG. 22 is a cross-sectional view of the semiconductor sensor chip of FIG. 21, FIGS. 22A, 22B, and 22C being taken along lines A-A, B-B, and C-C in FIG. 21, respectively.
Figure 22:
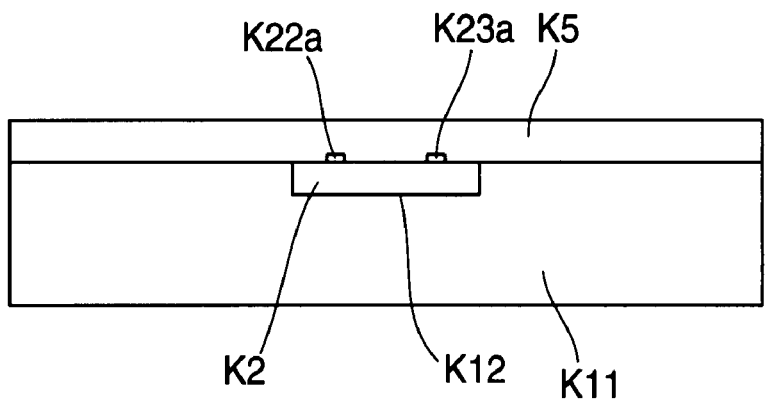
Figure 22:
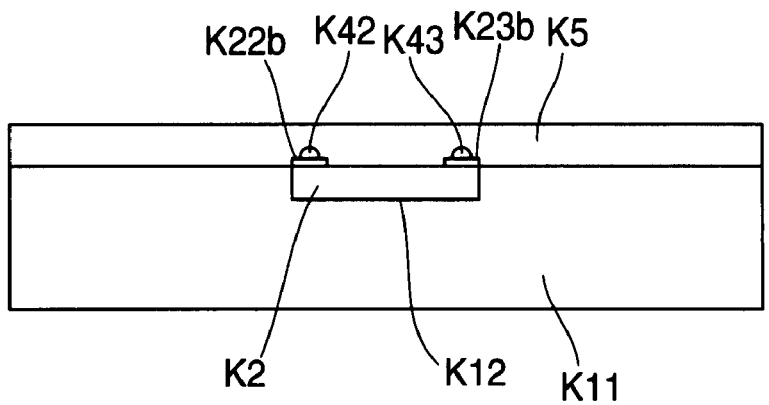
Figure 23:
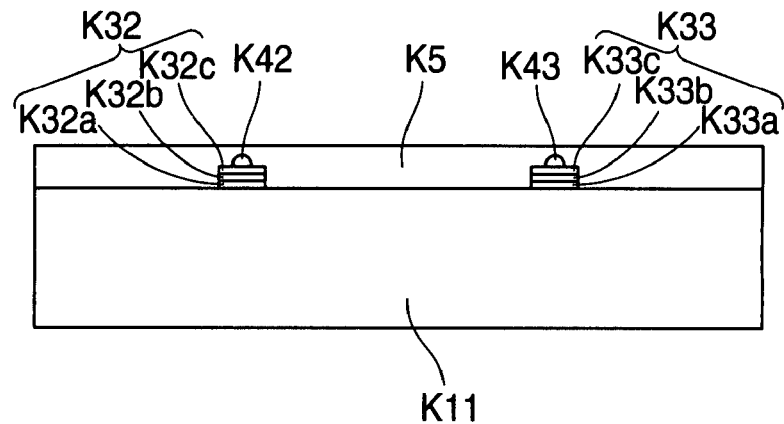
FIG. 23 is a cross-sectional view of the semiconductor sensor chip of FIG. 21, FIGS. 23A, 23B, and 23C being taken along lines D-D, E-E, and F-F in FIG. 21, respectively.
Figure 23:
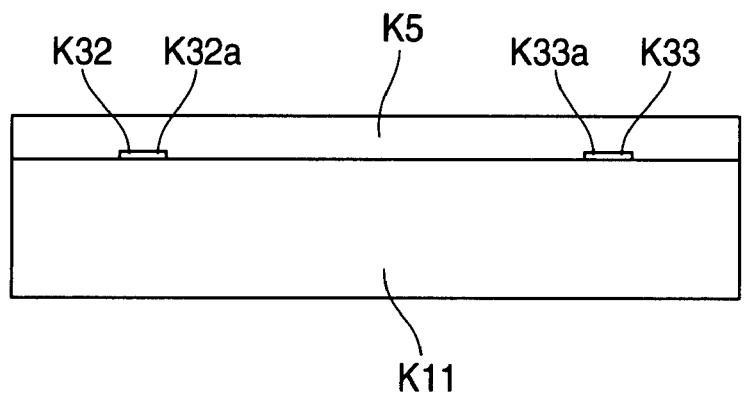
Figure 23:
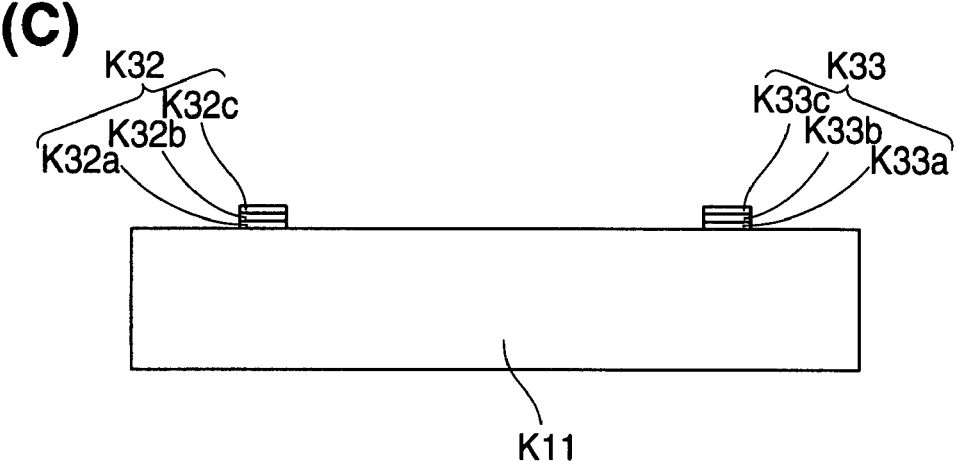

The FET chips which can be used in the semiconductor sensor chip according to the second aspect of the invention include FETs of the structure reported by the inventors in JP-A 2004-4007 (Patent Reference 1) and Jpn. J. Appl. Phys., Vol. 43, No. 1A/B, 2004, pp. L105-107 (Non-Patent Reference 1), for example. One exemplary FET chip is constructed, as shown in FIG. 20A, such that a gate dielectric layer K21 in the form of a silicon oxide film or the like, a source electrode K22, and a drain electrode K23 lie in sequence on a silicon substrate K20, and channel regions K24, K24 are formed below source electrode K22 and source electrode K23, respectively, wherein the presence or absence and the quantity of a substance under test are detected as changes of surface potential measurable on the electrode sides via channel regions K24, K24 disposed below source electrode K22 and source electrode K23, respectively. Illustrated in FIG. 20 are a field oxide film K25 and a protective oxide film K26. The above-described FET according to the first aspect of the invention is also preferable.

In implementing semiconductor sensing using such FET, for example, a semiconductor sensing system is constructed as shown in FIG. 20B, wherein an organic monomolecular film K27 is provided on gate dielectric layer K21 of the FET as a direct detector section, a gate electrode K28 is provided close to organic monomolecular film K27, and gate electrode K28 and source and drain electrodes K22 and K23 are connected through a power supply and a measuring instrument such as an ammeter. Sensing is possible when a test liquid "s" is brought in contact with both organic monomolecular film K27 and gate electrode K28. The semiconductor sensor chip according to the second aspect of the invention is constructed such that the sensor section of the semiconductor sensing system, that is, FET and part of wiring connected to each of the source and drain electrodes are separated from the meter section so that the sensor section may be attached to and detached from the meter section. Note that in FIG. 20B, "a" denotes an ammeter, "e" denotes ground or earth, and "p" denotes a DC power supply.

The semiconductor sensor chip according to the second aspect of the invention does not include a section to function as a measuring instrument (including a power supply and a meter), but is basically composed of a FET chip, and a source electrode terminal wiring and a drain electrode terminal wiring which are essential as a sensor section. Accordingly, this semiconductor sensor chip allows for more practical disposal of the sensor section. Also since the FET which is a microscopic precision part and the fine source electrode terminal wiring and drain electrode terminal wiring connected thereto are sealed with an encapsulant or with a board on which the FET chip, the source electrode terminal wiring, and the drain electrode terminal wiring are disposed and an encapsulant, the semiconductor sensor chip is endowed with a sufficient strength necessary to handle it.

In the semiconductor sensor chip according to the second aspect of the invention, the gate dielectric layer of the FET which should be exposed to the outside for its function, the source electrode terminal wiring and the drain electrode terminal wiring constituting a conductive path for electric signals detected by the semiconductor sensor chip to a measuring instrument are exposed to the outside. By connecting ends of the source electrode terminal wiring and the drain electrode terminal wiring to electric signal input/output terminals, a semiconductor sensing system including the sensor section and the measuring instrument section is constructed. Semiconductor sensing becomes possible when an organic monomolecular film is formed on the gate dielectric layer of the FET as a direct detector section and the detector section is contacted with a test liquid.

Now referring to the drawings, preferred embodiments of the semiconductor sensor chip according to the second aspect of the invention are described in detail.

Description starts with a first preferred embodiment of the semiconductor sensor chip according to the second aspect of the invention. In the first embodiment, a semiconductor sensor chip comprises a FET chip having a gate dielectric layer, a source electrode, and a drain electrode integrated on a silicon substrate, the FET chip being buried in a recess on a board, a source electrode terminal wiring pattern connected to the source electrode through one lead wire, and a drain electrode terminal wiring pattern connected to the drain electrode through another lead wire, the wiring patterns being formed on the board. The FET chip, the source electrode terminal wiring pattern, the drain electrode terminal wiring pattern, and the one and other lead wires are sealed between the upper surface of the board and an encapsulant layer such that the gate dielectric layer of the FET chip, an end portion of the source electrode terminal wiring pattern which is not connected to the source electrode, and an end portion of the drain electrode terminal wiring pattern which is not connected to the drain electrode are exposed.

FIGS. 21 to 24 illustrate one example of this first embodiment. The semiconductor sensor chip K1 includes a FET chip K2, a source electrode terminal wiring pattern K32, a drain electrode terminal wiring pattern K33, a lead wire (one lead wire) K42, and a lead wire (other lead wire) K43 arranged on a board K11, which are sealed with an encapsulant layer K5 and between board K11 and encapsulant layer K5. The first embodiment is suited in either of the use where the detector section is immersed in liquid and the use where liquid is dripped on the detector section.

The board K11 is a small plate-shaped piece while a glass epoxy board is preferably used from the standpoints of wiring pattern formation, processability and the like. The board K11 is provided with a recess (facing) K12 having a depth approximate to the thickness of FET chip K2 for allowing FET chip K2 to be buried therein. The FET chip K2 is buried in recess K12 by suitable means such as die bonding.

Figure 24:
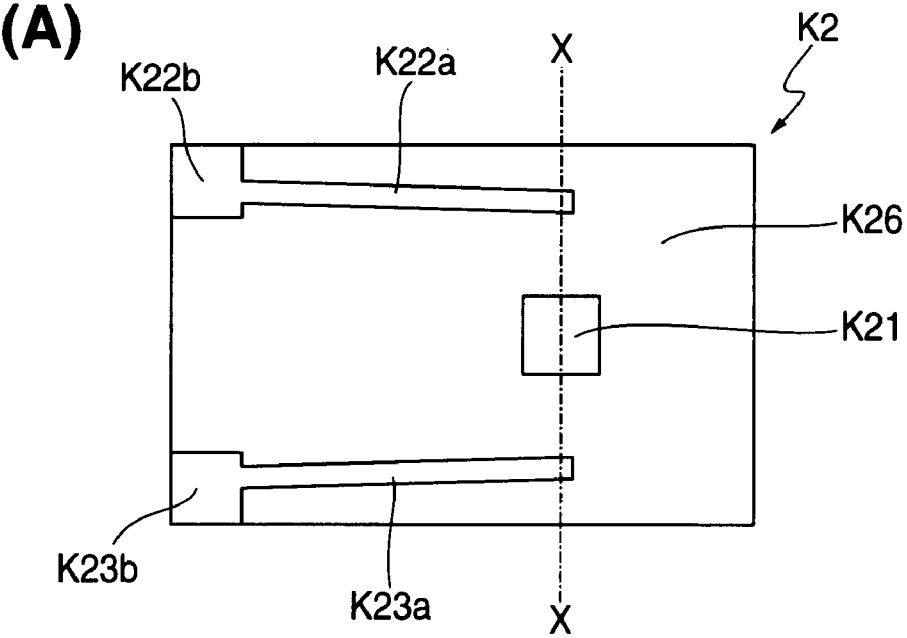
FIG. 24 is a view of a FET chip of the semiconductor sensor chip of FIG. 21, FIG. 24A being a plan view, FIG. 24B being a side elevation, and FIG. 24C being a cross-sectional view taken along lines X-X in FIG. 24A.
Figure 24:
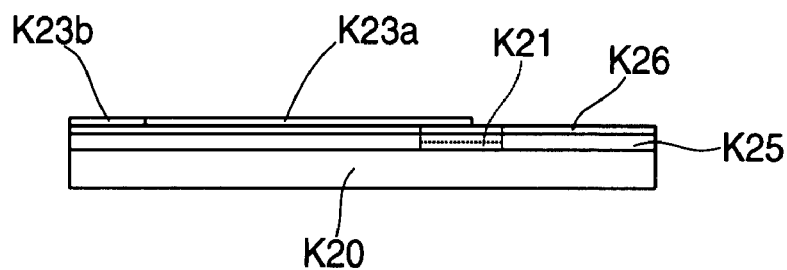
Figure 24:
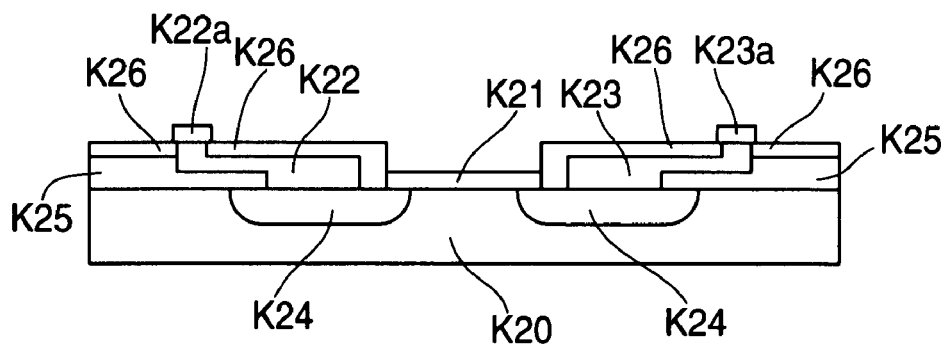

In the second aspect of the invention, the FET chip in the semiconductor sensor chip may be the above-described one. In this example of semiconductor sensor chip, as shown in FIG. 24, source electrode K22 and drain electrode K23 are connected to one ends of wiring patterns (aluminum wiring patterns) K22a, K23a extending over the upper surface of FET chip K2 and formed on the upper surface of FET chip K2, and the other ends of wiring patterns (aluminum wiring patterns) K22a, K23a are formed as bonding pads (aluminum pads) K22b, K23b for connection to lead wires K42, K43, respectively. The bonding pads K22b, K23b are connected to lead wires K42, K43, respectively. Illustrated in FIGS. 21 to 24 are a silicon substrate K20, a gate dielectric layer K21, channel regions K24, a field oxide film K25, and a protective oxide film K26.

Also formed on board K11 are a source electrode terminal wiring pattern K32 and a drain electrode terminal wiring pattern K33. In this case, source electrode terminal wiring pattern K32 and drain electrode terminal wiring pattern K33 are based on copper conductor patterns K32a, K33a, while opposite end portions of copper conductor patterns K32a, K33a are overlaid with Ni-P layers K32b, K33b and gold layers K32c, K33c. Such wiring patterns can be formed by prior art well-known techniques such as plating. Lead wires K42, K43 bridge between gold layers K32c, K33c at the FET chip K2 side end of source electrode terminal wiring pattern K32 and drain electrode terminal wiring pattern K33 and bonding pads (aluminum pads) K22b, K23b to provide connection therebetween. Joints of lead wires K42, K43 can be formed by a wire bonding technique.

The FET chip K2, source electrode terminal wiring pattern K32, drain electrode terminal wiring pattern K33, and lead wires K42, K43 are sealed between the upper surface of board K11 and encapsulant layer K5 such that the gate dielectric layer K21 of FET chip K2, an end portion of source electrode terminal wiring pattern K32 which is not connected to lead wire (one lead wire) K42, and an end portion of drain electrode terminal wiring pattern K32 which is not connected to lead wire (other lead wire) K43 are exposed. A detector section is formed on the area of gate dielectric layer K21 which is not sealed, as will be described later, and the exposed end portions of source electrode terminal wiring pattern K32 and drain electrode terminal wiring pattern K33 which are not sealed are connected to electric signal input/output terminals of a measuring instrument to be described later.

Using the semiconductor sensor chip described above, a semiconductor sensing system can be constructed which comprises the semiconductor sensor chip and a measuring instrument having electric signal input/output terminals which are detachably connected to the exposed portions of the source electrode terminal wiring pattern and the drain electrode terminal wiring pattern of the semiconductor sensor chip directly or via anisotropic conductive rubber, the measuring instrument being connected to the semiconductor sensor chip for measuring the electric signal detected by the FET chip. Herein, for connection between the semiconductor sensor chip and the measuring instrument body, a method capable of forming a joint with water- and liquid-proofness, for example, sealing with an O-ring, is applicable, and the joint may be secured using screws and clamps.

In particular, anisotropic conductive rubber is preferably used for connection between the exposed portions of the source electrode terminal wiring pattern and the drain electrode terminal wiring pattern of the semiconductor sensor chip and the electric signal input/output terminals of the measuring instrument. When the connection is accomplished by sandwiching anisotropic conductive rubber between the exposed portions of the source electrode terminal wiring pattern and the drain electrode terminal wiring pattern and the electric signal input/output terminals of the measuring instrument, not only electric conduction is ensured by the conductivity of anisotropic conductive rubber, but also the anisotropic conductive rubber affords closer contact due to its elasticity and a buffer action for the compressive force of connecting in close contact the semiconductor sensor chip which is less resistant to external forces. Then more reliable and stable conduction is established between the sensor chip and the measuring instrument.

Described below is a second preferred embodiment of the semiconductor sensor chip according to the second aspect of the invention.

In the second embodiment, a semiconductor sensor chip comprises a FET chip having a gate dielectric layer, a source electrode, and a drain electrode integrated on a silicon substrate, the FET chip being buried in a recess on a board, a source electrode terminal wiring pattern connected to the source electrode through one lead wire, and a drain electrode terminal wiring pattern connected to the drain electrode through another lead wire, the wiring patterns being formed on the board. The FET chip, the source electrode terminal wiring pattern, the drain electrode terminal wiring pattern, and the one and other lead wires are sealed between the upper surface of the board and an encapsulant layer such that the gate dielectric layer of the FET chip is exposed. The source electrode terminal wiring pattern includes an interconnecting extension which passes through the board in its thickness direction, connects to the source electrode terminal wiring pattern, and includes an end portion exposed on the lower surface side of the board, and the drain electrode terminal wiring pattern includes an interconnecting extension which passes through the board in its thickness direction, connects to the drain electrode terminal wiring pattern, and includes an end portion exposed on the lower surface side of the board.

FIGS. 25 to 28 illustrate one example of this second embodiment. The semiconductor sensor chip K1 includes a FET chip K2, source electrode terminal wiring patterns K32, K32, drain electrode terminal wiring patterns K33, K33, lead wires (one lead wires) K42, K42, and lead wires (other lead wires) K43, K43 arranged on a board K11, which are sealed with an encapsulant layer K5 and between board K11 and encapsulant layer K5. The second embodiment is especially suited in the use where liquid is dripped on the detector section.

The board K11 is a small plate-shaped piece while a glass epoxy board is preferably used from the standpoints of wiring pattern formation, processability and the like. The board K11 is provided with a recess (facing) K12 having a depth approximate to the thickness of FET chip K2 for allowing FET chip K2 to be buried therein. The FET chip K2 is buried in recess K12 by suitable means such as die bonding.

Figure 25:
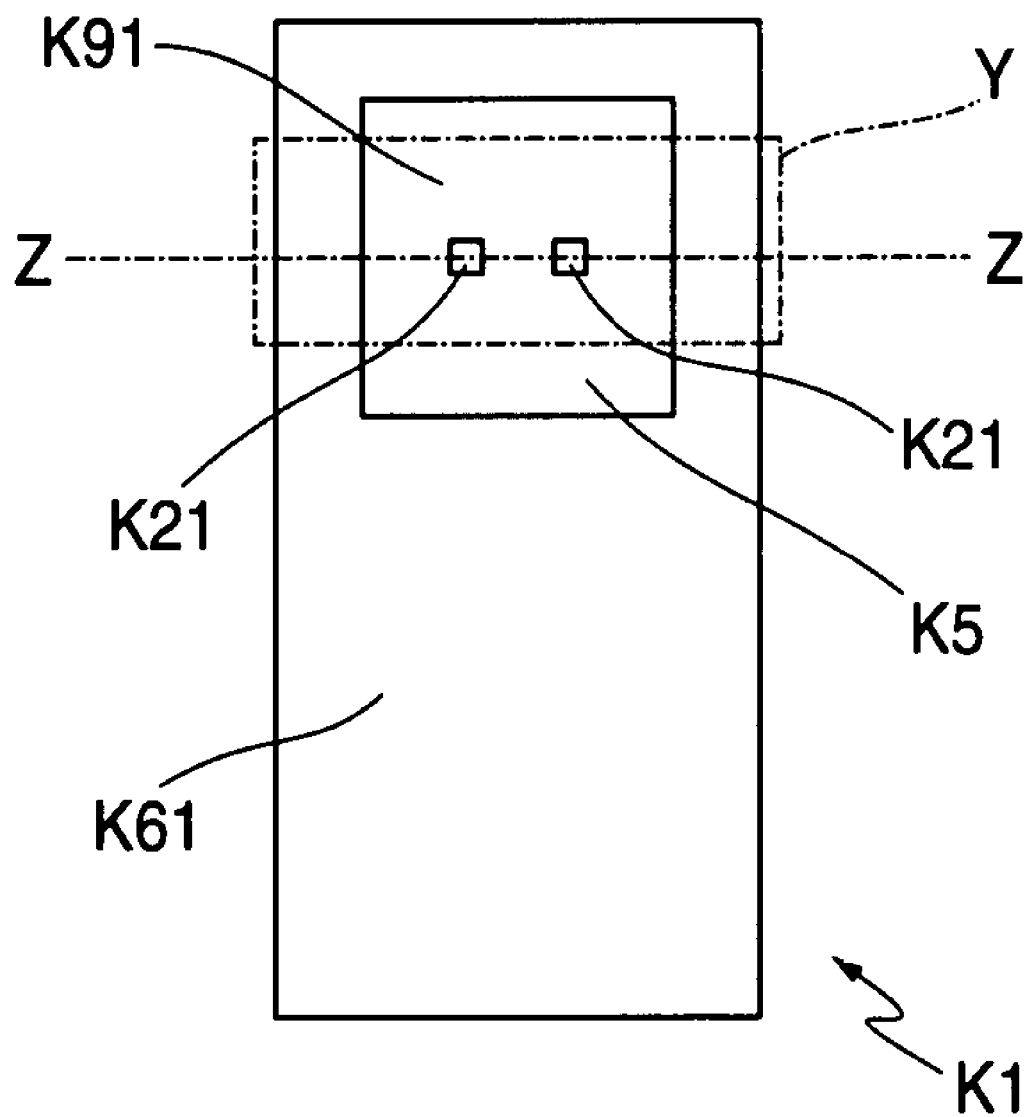
FIG. 25 is a plan view showing one example in a second embodiment of the semiconductor sensor chip according to the invention (second aspect).
Figure 26:
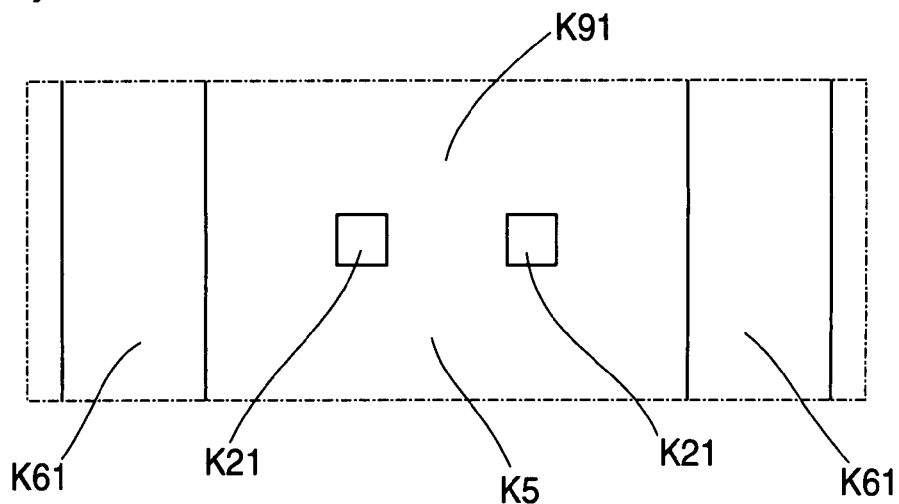
FIG. 26 is an enlarged view of the semiconductor sensor chip of FIG. 25, FIG. 26A being an enlarged plan view of a section Y in FIG. 25 and FIG. 26B being a plan view of the state prior to sealing with an encapsulant layer (or with the encapsulant layer removed).
Figure 26:
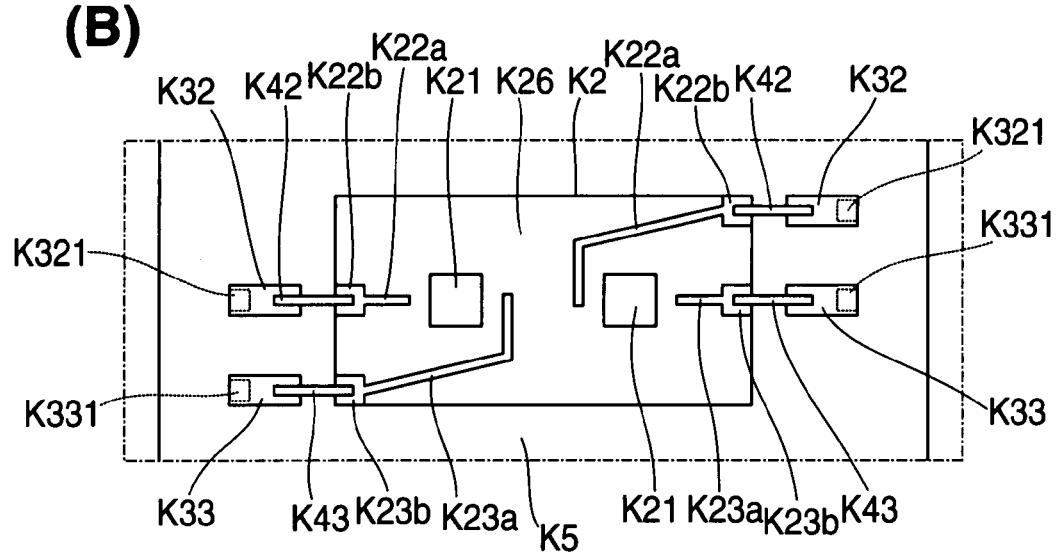
Figure 27:
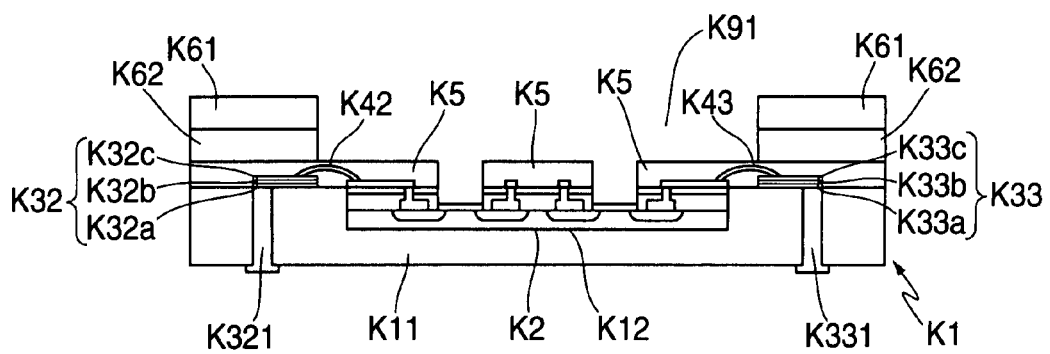
FIG. 27 illustrates the semiconductor sensor chip of FIG. 25 and a measuring instrument connected thereto, FIG. 27A being a cross-sectional view taken along lines Z-Z in FIG. 25, FIG. 27B being an enlarged cross-sectional view of the FET chip of FIG. 27A, and FIG. 27C being a cross-sectional view showing the semiconductor sensor chip of FIG. 27A and a measuring instrument connected thereto.
Figure 27:
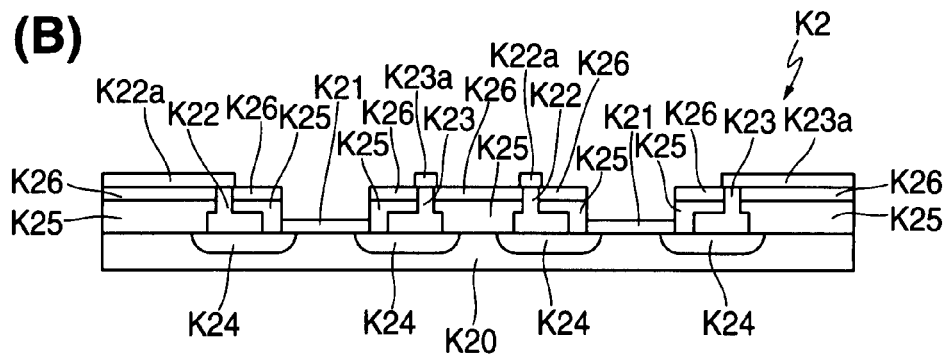
Figure 27:
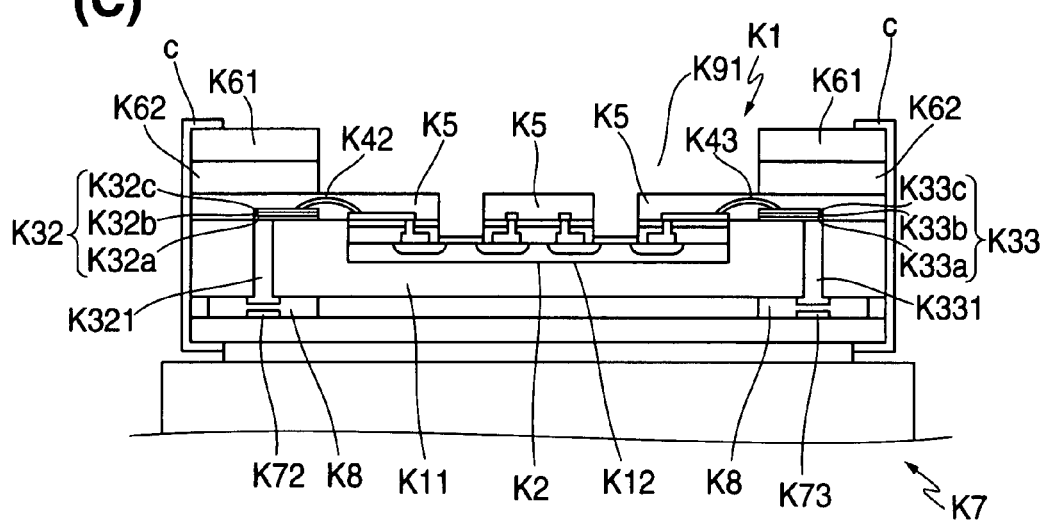

In the second aspect of the invention, the FET chip in the semiconductor sensor chip may be the above-described one. In this example of semiconductor sensor chip, as shown in FIG. 26B, two gate dielectric layers K21, K21 are formed on FET chip K2. The source electrodes K22, K22 and drain electrodes K23, K23 are connected to one ends of wiring patterns (aluminum wiring patterns) K22a, K22a, K23a, K23a extending over the upper surface of FET chip K2 and formed on the upper surface of FET chip K2, and the other ends of wiring patterns (aluminum wiring patterns) K22a, K22a, K23a, K23a are formed as bonding pads (aluminum pads) K22b, K22b, K23b, K23b for connection to lead wires K42, K42, K43, K43, respectively. The bonding pads K22b, K22b, K23b, K23b are connected to lead wires K42, K42, K43, K43, respectively. Illustrated in FIGS. 25 to 27 are a silicon substrate K20, channel regions K24, a field oxide film K25, and a protective oxide film K26.

Also formed on board K11 are source electrode terminal wiring patterns K32, K32 and drain electrode terminal wiring patterns K33, K33. In this case, source electrode terminal wiring patterns K32, K32 and drain electrode terminal wiring patterns K33, K33 are based on copper conductor patterns K32a, K32a, K33a, K33a; and copper conductor patterns K32a, K32a, K33a, K33a are, in turn, overlaid with Ni-P layers K32b, K32b, K33b, K33b and gold layers K32c, K32c, K33c, K33c. Such wiring patterns can be formed by prior art well-known techniques such as plating. Lead wires K42, K42, K43, K43 connect gold layers K32c, K32c, K33c, K33c at the FET chip K2 side ends of source electrode terminal wiring patterns K32, K32 and drain electrode terminal wiring patterns K33, K33 to bonding pads (aluminum pads) K22b, K22b, K23b, K23b. Joints of these lead wires can be formed by a wire bonding technique.

The FET chip K2, source electrode terminal wiring patterns K32, K32, drain electrode terminal wiring patterns K33, K33, and lead wires K42, K42, K43, K43 are sealed between the upper surface of board K11 and encapsulant layer K5 such that the gate dielectric layers K21, K21 of FET chip K2 are exposed. A detector section is formed on the area of gate dielectric layer K21 which is not sealed, as will be described later.

In the second embodiment, source electrode terminal wiring patterns K32, K32 includes interconnecting extensions K321, K321 which each passes through board K11 in its thickness direction, connects to the lower surface (copper conductor patterns K32a, K32a) of the source electrode terminal wiring pattern, and includes an end portion exposed on the lower surface side of board K11, and drain electrode terminal wiring patterns K33, K33 include interconnecting extensions K331, K331 which each passes through board K11 in its thickness direction, connects to the lower surface (copper conductor patterns K33a, K33a) of the drain electrode terminal wiring pattern, and includes an end portion exposed on the lower surface side of board K11. The exposed end portions of interconnecting extensions K321, K321 from the source electrode terminal wiring patterns and interconnecting extensions K331, K331 from the drain electrode terminal wiring patterns are formed in pad shape. The exposed end portions (pad-shaped terminals) of interconnecting extensions K321, K321 from the source electrode terminal wiring patterns and interconnecting extensions K331, K331 from the drain electrode terminal wiring patterns are connected to electric signal input/output terminals of a measuring instrument to be described later.

Using the semiconductor sensor chip described above, a semiconductor sensing system can be constructed which comprises the semiconductor sensor chip and a measuring instrument having electric signal input/output terminals which are detachably connected to the exposed portions of the interconnecting extension from the source electrode terminal wiring pattern and the interconnecting extension from the drain electrode terminal wiring pattern of the semiconductor sensor chip directly or via anisotropic conductive rubber, the measuring instrument being connected to the semiconductor sensor chip for measuring the electric signal detected by the FET chip. Herein, for connection between the semiconductor sensor chip and the measuring instrument body, a method capable of forming a joint with water- and liquid-proofness, for example, sealing with an O-ring, is applicable, and the joint may be secured using screws and clamps.

In particular, anisotropic conductive rubber is preferably used for connection between the exposed portions of the interconnecting extension from the source electrode terminal wiring pattern and the interconnecting extension from the drain electrode terminal wiring pattern of the semiconductor sensor chip and the electric signal input/output terminals of the measuring instrument. When the connection is accomplished by sandwiching anisotropic conductive rubber between the exposed portions of the interconnecting extension from the source electrode terminal wiring pattern and the interconnecting extension from the drain electrode terminal wiring pattern and the electric signal input/output terminals of the measuring instrument, not only electric conduction is ensured by the conductivity of anisotropic conductive rubber, but also the anisotropic conductive rubber affords closer contact due to its elasticity and a buffer action for the compressive force of connecting in close contact the semiconductor sensor chip which is less resistant to external forces. Then more reliable and stable conduction is established between the sensor chip and the measuring instrument.

Specifically, as shown in FIG. 27C, anisotropic conductive rubbers K8, K8, K8, K8 are disposed between interconnecting extensions K321, K321 from the source electrode terminal wiring pattern and interconnecting extensions K331, K331 from the drain electrode terminal wiring pattern of semiconductor sensor chip K1 and electric signal input/output terminals K72, K72, K73, K73 of measuring instrument K7 located in register therewith, after which semiconductor sensor chip K1 and measuring instrument K7 are compressed from opposite sides, thereby bringing in close contact interconnecting extensions K321, K321 from the source electrode terminal wiring pattern, interconnecting extensions K331, K331 from the drain electrode terminal wiring pattern, anisotropic conductive rubbers K8, K8, K8, K8, and electric signal input/output terminals K72, K72, K73, K73. This establishes conduction between semiconductor sensor chip K1 and measuring instrument K7. In FIG. 27C, "c" denotes clamps for retaining a force of clamping semiconductor sensor chip K1 and detector K7 together.

In the first and second embodiments described above, the FET chip is buried in a recess formed on a board, and a source electrode terminal wiring and a drain electrode terminal wiring are formed on the board as a wiring pattern. Then the surface to be sealed with the encapsulant is substantially flat. Thus, the method of sealing with encapsulant employed for the semiconductor sensor chip described above may a method involving applying a UV-curable resin composition, for example, by such techniques as screen printing, and curing the composition.

Also, in the first and second embodiments described above, when the semiconductor sensor chip is used in the mode of dripping a liquid onto the detector section, it is also preferable that a liquid reservoir (dipping area) be provided on the encapsulant layer.

Specifically, as shown in FIGS. 25 to 27, a weir layer K61 is laid on encapsulant layer K5 of semiconductor sensor chip K1 surrounding the exposed areas of gate dielectric layers K21, K21, so as to define a liquid reservoir K91 having a predetermined volume. Particularly when semiconductor sensor chip K1 and measuring instrument K7 are compressed from opposite sides to make connection between the wiring pattern or interconnecting extension therefrom and electric signal input/output terminals, as shown in FIG. 27, it is preferred to provide a rubber layer K62 between weir layer K61 and encapsulant layer K5 because it can impart a shock absorbing function to the semiconductor sensor device against the compression force applied for achieving connection between end portions of interconnecting extensions K321, K321 from the source electrode terminal wiring pattern and interconnecting extensions K331, K331 from the drain electrode terminal wiring pattern and electric signal input/output terminals K72, K72, K73, K73.

It is also preferable that a cavity K92 having a predetermined volume be formed on encapsulant layer K5 of semiconductor sensor chip K1 surrounding the exposed areas of gate dielectric layers K21, K21, the cavity becoming a flowpath for the test liquid.

Figure 28:
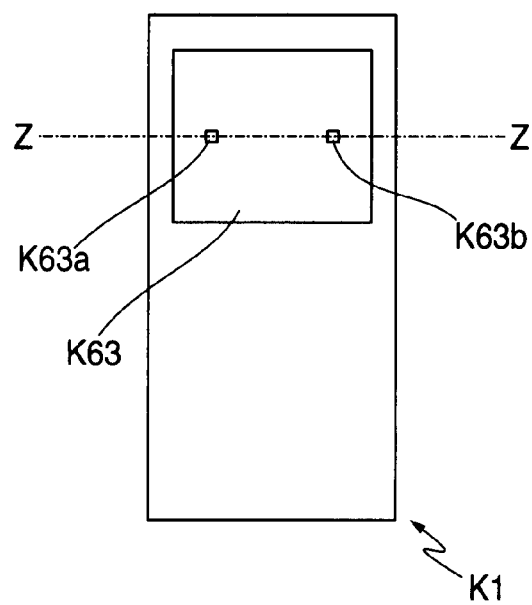
FIG. 28 illustrates another example in the second embodiment of the semiconductor sensor chip according to the invention (second aspect), FIG. 28A being a plan view and FIG. 28B being a cross-sectional view taken along lines Z-Z in FIG. 28A.
Figure 28:
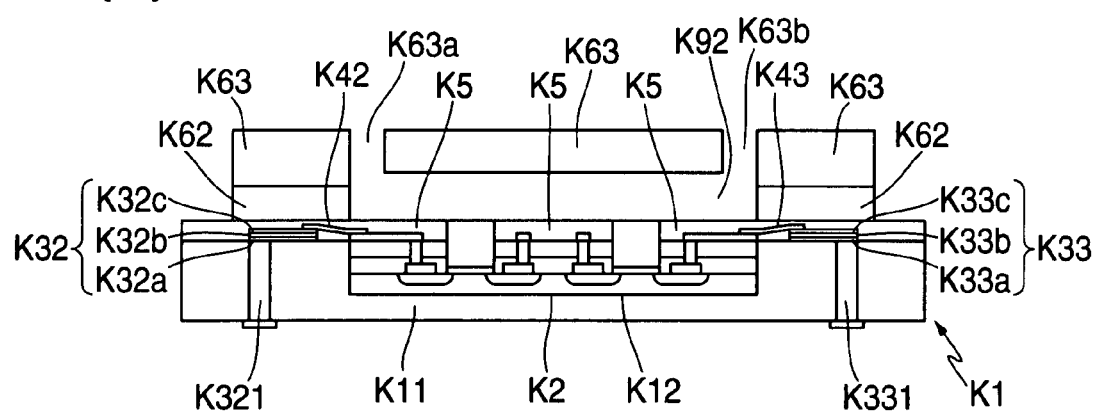

Specifically, as shown in FIG. 28, a lid K63 is provided on encapsulant layer K5 of semiconductor sensor chip K1 including the exposed areas of gate dielectric layers K21, K21, for defining a cavity K92 having an inlet port K63a and an outlet port K63b, the cavity becoming a flowpath for the test liquid. This allows the test liquid to continuously flow on and contact with the detector section of the semiconductor sensor chip. It is noted that like the above-described weir layer K61, a shock absorbing function can also be imparted in this case by providing a rubber layer K62 on the encapsulant layer K5 side of lid K63 as shown in FIG. 28. In FIG. 28, the same parts as in FIGS. 25 to 27 are designated by like numerals and their description is omitted.

A further preferred embodiment of the semiconductor sensor chip according to the second aspect of the invention is that of catheter type shown in FIGS. 29A and 29B. In this embodiment, a FET chip K2, a source electrode terminal wiring K320 connected to the source electrode (not shown), and a drain electrode terminal wiring K330 connected to the drain electrode (not shown) are sealed with an encapsulant K50 such that gate dielectric layer K21 of transistor chip K2, an end portion of source electrode terminal wiring K320 which is not connected to the source electrode (not shown), and an end portion of drain electrode terminal wiring K330 which is not connected to the drain electrode (not shown) are exposed. It is noted that in FIGS. 29A and 29B, "w" denotes a core shaft of the catheter.

In the case of the semiconductor sensor chip of catheter type, the FET may be the above-described one. However, since connections of the source electrode and source electrode wiring, and the drain electrode and drain electrode wiring should preferably be located at the center of the catheter, it is preferred that the FET have a source electrode through wiring which passes through the silicon substrate in a thickness direction and has one end connected to the source electrode and another end exposed on the lower surface side of the silicon substrate, and a drain electrode through wiring which passes through the silicon substrate in a thickness direction and has one end connected to the drain electrode terminal and another end exposed on the lower surface side of the silicon substrate, wherein a connection of the source electrode to the source electrode wiring and a connection of the drain electrode to the drain electrode wiring are disposed on the lower surface side of the silicon substrate.

Figure 29:
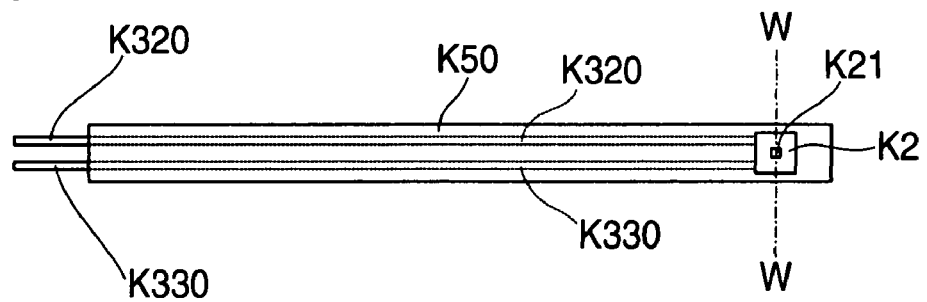
FIG. 29 illustrates a semiconductor sensor chip (catheter type semiconductor sensor chip) in another embodiment of the invention (second aspect), FIG. 29A being a plan view, FIG. 29B being a cross-sectional view taken along lines W-W in FIG. 29A, and FIG. 29C being a cross-sectional view of a FET chip.
Figure 29:
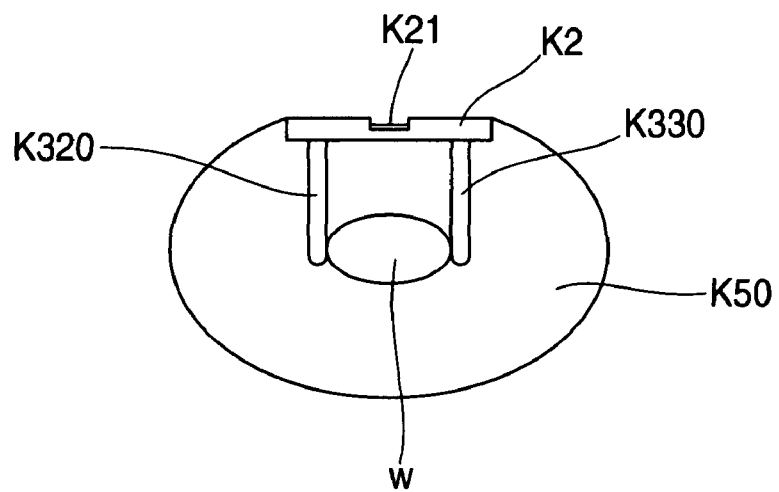
Figure 29:
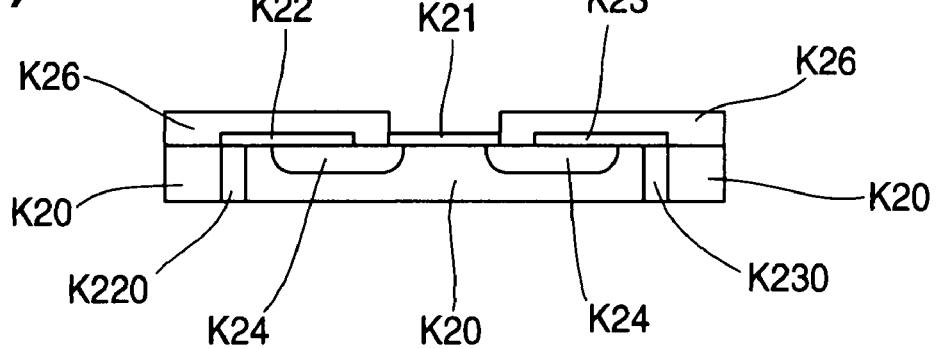

One specific example is a transistor, as shown in FIG. 29C, having a source electrode through wiring K220 which passes through silicon substrate K20 in its thickness direction and has one end connected to the lower surface of source electrode K22 and another end exposed on the lower surface side of silicon substrate K20, and a drain electrode through wiring K230 which passes through silicon substrate K20 in its thickness direction and has one end connected to the lower surface of drain electrode K23 and another end exposed on the lower surface side of silicon substrate K20. Illustrated in FIG. 29 are a gate dielectric layer K21, channel regions K24, and a protective oxide film K26.

The semiconductor sensor chip of catheter type as described above is capable of rapidly measuring changes of components in blood flow through a blood vessel in a real-time fashion, for example, measuring changes of pH, carbon dioxide concentration and oxygen concentration or increments or decrements of certain bio-substances in blood in a real-time fashion.

When semiconductor sensing is carried out using the semiconductor sensor chip according to the second aspect of the invention, as shown in FIG. 20B, an organic monomolecular film K27 is formed on gate dielectric layer K21 of FET chip K2 as a direct detector section, and a test liquid "s" is contacted with the detector section. Then the assembly is ready for sensing. For sensing, gate electrode K28 is provided in contact with the test liquid "s".

As described above, by using the FET according to the invention and forming an organic monomolecular film on its gate dielectric layer locally at a site to come in contact with the liquid surface, a semiconductor sensing device can be constructed in which the organic monomolecular film serves as a direct detector section. This enables semiconductor sensing on the basic principle of detecting as electrical signals changes of surface potential due to ion adsorption, bio-reaction or the like on the surface.

It is noted that the organic monomolecular film may be modified with DNA, enzyme, immunity or the like. It is also possible to use reporter molecules if necessary.

The preferred organic monomolecular film is an organic silane monomolecular film, which can be formed by patterning by a suitable patterning technique.

Using organic silane molecules, an organic silane monomolecular film can be formed on the gate dielectric layer by vapor phase chemical reaction or liquid phase reaction. By optimizing the organic silane monomolecular film, a closest packed film is formed.

The organic silane monomolecular films used herein include monomolecular films of alkoxysilanes having straight hydrocarbon radicals (e.g., alkyl radicals) of 3 to 20 carbon atoms containing at least one amino functional radical ($NH_2$—, —NH—, $C_5H_5N$—, $C_4H_4N$—, etc.) or carboxyl functional radical (—COOH, etc.), and monomolecular films of alkoxysilanes having non-reactive straight alkyl radicals or fluorinated alkyl radicals of 8 to 20 carbon atoms.

The incorporation of reactive functional radicals such as amino and carboxyl functional radicals may be implemented, aside from using alkoxysilanes having such functional radicals, by once forming a monomolecular film using alkoxysilanes having radicals which can be replaced by such functional radicals, for example, amino-inducible radicals such as —Br or —CN, then replacing the amino-inducible radicals by amino radicals.

Of the alkoxysilanes, trialkoxysilanes are preferred for adhesion and other properties, and the preferred alkoxy radicals are alkoxy radicals of 1 to 4 carbon atoms, especially methoxy and ethoxy radicals.

Illustrative examples of the alkoxysilane include $NH_2(CH_2)_3Si(OC_2H_5)_3$, $CH_3(CH_2)_{17}Si(OCH_3)_3$, and $CF_3(CF_2)_7(CH_2)_2Si(OCH_3)_3$.

In the second aspect of the invention, the sensor chip and the measuring instrument are readily attached or detached. Then the measuring instrument can be continuously used while the inexpensive sensor chip is disposable. The system is advantageously used in the application where single cycle use is basic, typically in the medical application. The system is also applicable in a safe and hygienic manner to medical instrumentation, environmental measurement, food management, biochemical analysis (e.g., DNA analysis, protein analysis, cell analysis, secretion identification), and the like.

It is noted that although reference is made to embodiments having one or two detector sections in describing illustrative embodiments of the second aspect of the invention, a multiple design in which a multiplicity of detector sections are formed on a common silicon substrate is possible. Also, when sensing is performed using the semiconductor sensor chip according to the second aspect of the invention, the gate electrode is disposed in proximity to the organic monomolecular film. The gate electrode may be preformed integral with the semiconductor sensor chip. This is advantageous because the sensor section with gate electrode is disposable, facilitating the sensing operation.

The invention claimed is:

1. A semiconductor sensing field effect transistor comprising a gate dielectric layer formed on silicon, which is to be used as a semiconductor sensing device after an organic monomolecular film is formed directly on said gate dielectric layer as a direct detector section, characterized in that said gate dielectric layer has a multilayer structure including, in sequence, a first silicon oxide layer, a silicon nitride layer, and a second silicon oxide layer, a low resistance layer buried in the gate dielectric layer, and the organic monomolecular film is an organic silane monomolecular film.

2. A semiconductor sensing device having an organic monomolecular film/gate dielectric layer/semiconductor structure wherein the organic monomolecular film is formed on said gate dielectric layer of the semiconductor sensing field effect transistor of claim 1 as a direct detector section.

3. The semiconductor sensing field effect transistor of claim 1, wherein part of said silicon nitride layer is replaced by a low-resistance layer.

4. The semiconductor sensing device of claim 2, wherein the organic monomolecular film is an organic silane monomolecular film.

5. The semiconductor sensing device of claim 2, wherein part of said silicon nitride layer is replaced by a low-resistance layer.

6. The semiconductor sensing field effect transistor of claim 1, wherein the organic silane monomolecular film includes a monomolecular film of an alkoxysilane.

7. A semiconductor sensing field effect transistor comprising a gate dielectric layer formed on silicon, which is to be used as a semiconductor sensing device after an organic monomolecular film is formed directly on said gate dielectric layer as a direct detector section, characterized in that said gate dielectric layer has a multilayer structure including, in sequence, a first silicon oxide layer, a silicon nitride layer, and a second silicon oxide layer, a low resistance layer is buried in the gate dielectric layer, and the organic monomolecular film is formed using alkoxysilanes having radicals which can be replaced by functional radicals, and then replacing aminoinducible radicals by amino radicals.

8. The semiconductor sensing field effect transistor of claim 6, wherein said alkoxysilane in said organic monomolecular film is a trialkoxysilane.

9. The semiconductor sensing field effect transistor of claim 3, wherein said low-resistance layer includes an impurity-implanted layer, a metal silicide layer and a tungsten layer.

10. The semiconductor sensing field effect transistor of claim 6, wherein the alkoxysilane is $NH_2(CH_2)_3Si(OC_2H_5)_3$, or $CH_3(CH_2)_{17}Si(OCH_3)_3$, or $CF_3(CF_2)_7(CH_2)_2Si(OCH_3)_3$.

* * * * *